(12) United States Patent
Hitt et al.

(10) Patent No.: US 7,788,970 B2
(45) Date of Patent: Sep. 7, 2010

(54) WIRELESS SENSOR PROBE

(75) Inventors: Dale K. Hitt, San Jose, CA (US); Kurtis G. Heaton, Pleasanton, CA (US)

(73) Assignee: Digital Sun, Inc., San Jose, CA (US)

( * ) Notice: Subject to any disclaimer, the term of this patent is extended or adjusted under 35 U.S.C. 154(b) by 0 days.

(21) Appl. No.: 10/693,017

(22) Filed: Oct. 24, 2003

(65) Prior Publication Data

US 2004/0083833 A1    May 6, 2004

Related U.S. Application Data

(60) Provisional application No. 60/421,963, filed on Oct. 28, 2002.

(51) Int. Cl.
*G01N 25/56* (2006.01)

(52) U.S. Cl. .......................................................... 73/73

(58) Field of Classification Search ...................... 73/73, 73/84, 866; 239/63–74
See application file for complete search history.

(56) References Cited

U.S. PATENT DOCUMENTS

| | | | | |
|---|---|---|---|---|
| 3,783,804 | A | * | 1/1974 | Platz ..................... 239/DIG. 4 |
| 3,794,992 | A | | 2/1974 | Gehman |
| 4,184,789 | A | | 1/1980 | Gilde, Jr. |
| 4,445,788 | A | * | 5/1984 | Twersky et al. ................. 73/73 |
| 4,567,563 | A | | 1/1986 | Hirsch |
| 4,726,239 | A | | 2/1988 | Boggess et al. |
| 4,814,608 | A | * | 3/1989 | Dempsey et al. ............ 250/253 |
| 4,847,781 | A | | 7/1989 | Brown, III et al. |
| 4,852,802 | A | * | 8/1989 | Iggulden et al. ................ 239/64 |
| 5,150,622 | A | * | 9/1992 | Vollweiler ............... 73/864.74 |
| 5,209,129 | A | * | 5/1993 | Jaselskis et al. .......... 73/864.64 |
| 5,385,297 | A | | 1/1995 | Rein et al. |
| 5,408,893 | A | * | 4/1995 | McLeroy ................. 73/864.44 |
| 5,418,466 | A | * | 5/1995 | Watson et al. ................ 324/668 |
| 5,635,710 | A | * | 6/1997 | Reed et al. .................. 250/253 |
| 5,740,031 | A | | 4/1998 | Gagnon ...................... 364/145 |
| 5,813,606 | A | | 9/1998 | Ziff .............................. 239/67 |
| 6,275,500 | B1 | | 8/2001 | Callaway, Jr. et al. ....... 370/449 |
| 6,452,499 | B1 | | 9/2002 | Runge et al. ................. 340/601 |

(Continued)

FOREIGN PATENT DOCUMENTS

GB        2247951  A  *  3/1992

(Continued)

*Primary Examiner*—Hezron Williams
*Assistant Examiner*—Nashmiya S Fayyaz
(74) *Attorney, Agent, or Firm*—Inskeep IP Group, Inc.

(57) ABSTRACT

A wireless sensor probe for use in environmental monitoring and control includes a separable probe body and sensor mast. The probe body includes a void configured to house the sensor mast including one or more sensor devices for sensing a soil property surrounding the probe body when the probe body is inserted partially into the ground. The probe body includes a probe top part for encapsulating the probe body and the sensor mast. The sensor mast is inserted into the probe body to form the sensor probe. In another embodiment, a wireless sensor probe includes a housing containing one or more sensor devices. The probe further includes a collar situated near a top portion of the housing being used to anchor the housing to the top of the ground and a gasket formed on the outside perimeter of the housing for securing the housing in the ground.

23 Claims, 13 Drawing Sheets

U.S. PATENT DOCUMENTS

| | | | |
|---|---|---|---|
| 6,600,971 B1 | 7/2003 | Smith et al. | 700/284 |
| 6,601,440 B1 * | 8/2003 | Chuang | 73/73 |
| 6,752,362 B1 * | 6/2004 | Gretz | 248/156 |
| 7,240,743 B2 * | 7/2007 | Buss et al. | 175/58 |
| 7,281,439 B2 * | 10/2007 | Schmitt et al. | 73/863 |
| 2002/0112531 A1 * | 8/2002 | Hubbell et al. | 73/73 |
| 2002/0144453 A1 * | 10/2002 | Su | 43/124 |

FOREIGN PATENT DOCUMENTS

| | | | |
|---|---|---|---|
| JP | 2002168674 A | * | 6/2002 |
| WO | WO 2006001734 A1 | * | 1/2006 |

* cited by examiner

FIGURE 1 - PRIOR ART

Figure 3 - Message Routing

Figure 5 - Sensor Data Routing

Figure 6 - Transceiver Synchronization

Figure 7 - Diagram of Soil Probe

Figure 8 - Separable Probe Body

Figure 10 - Configuration and Dimensions of Probe Body
Figure 10A      Figure 10B
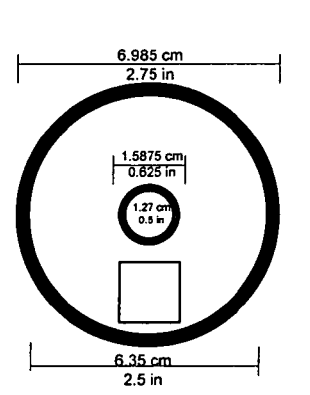
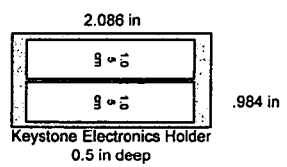
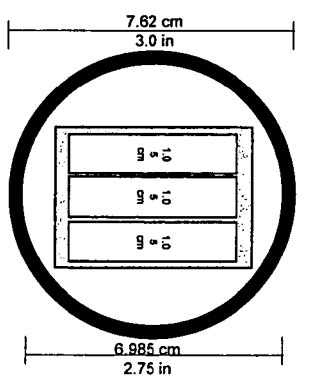
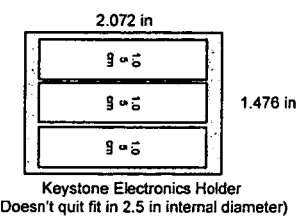
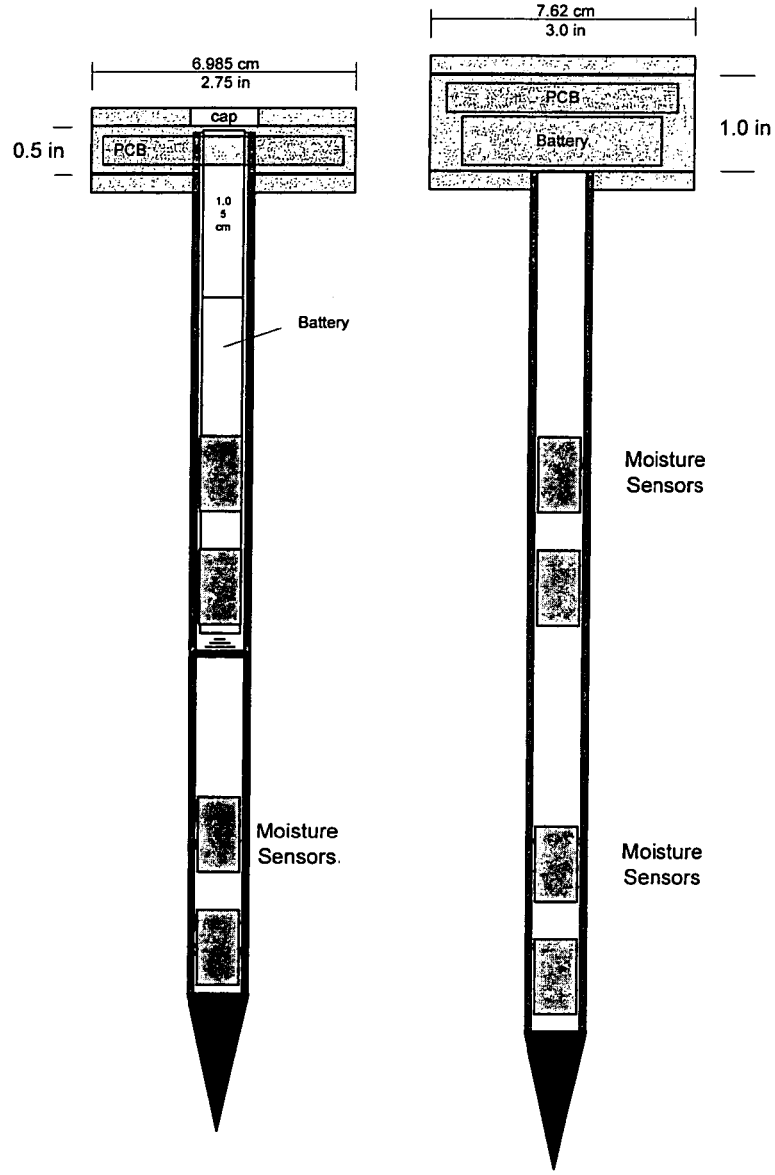

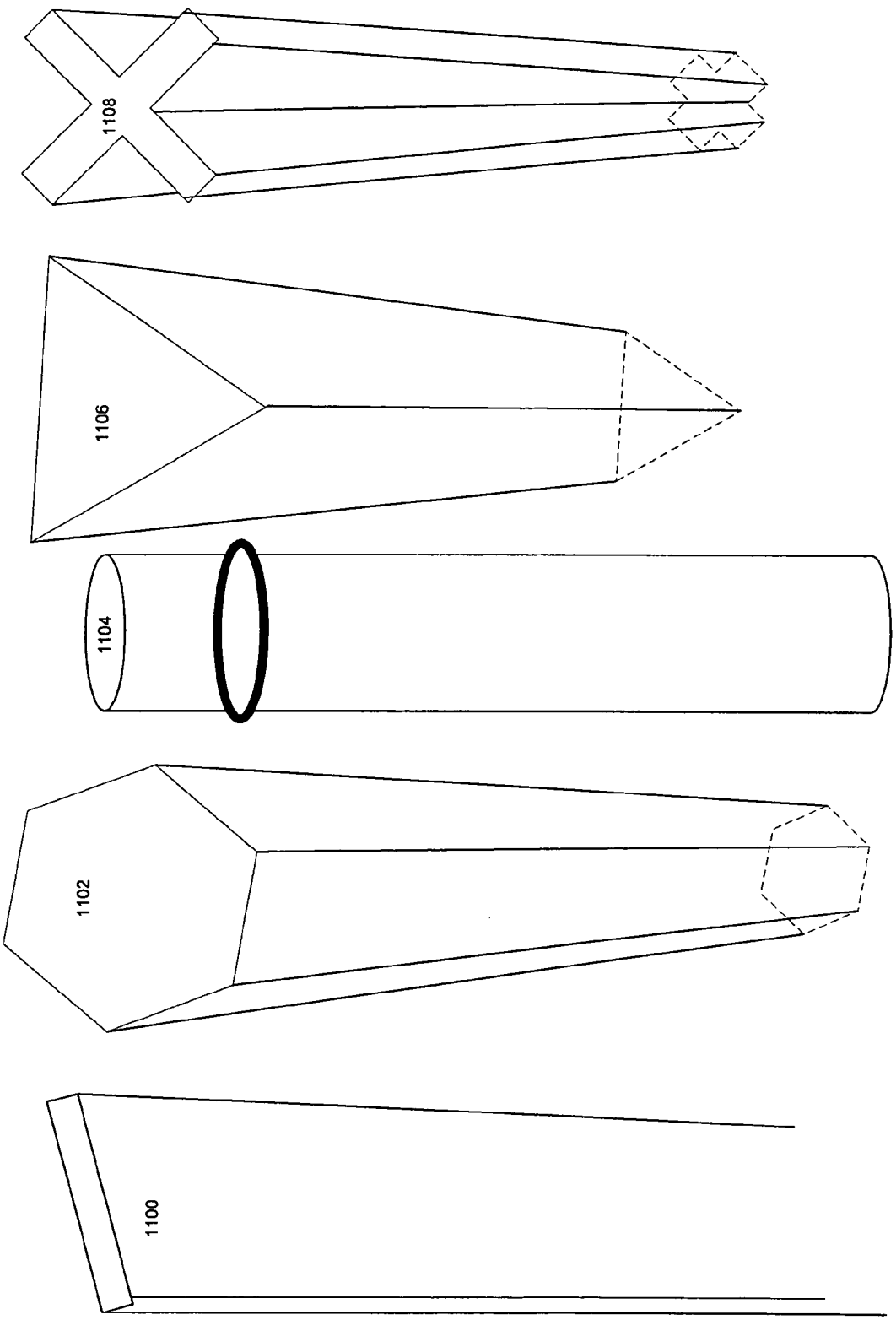
Figure 11 - Probe Shapes

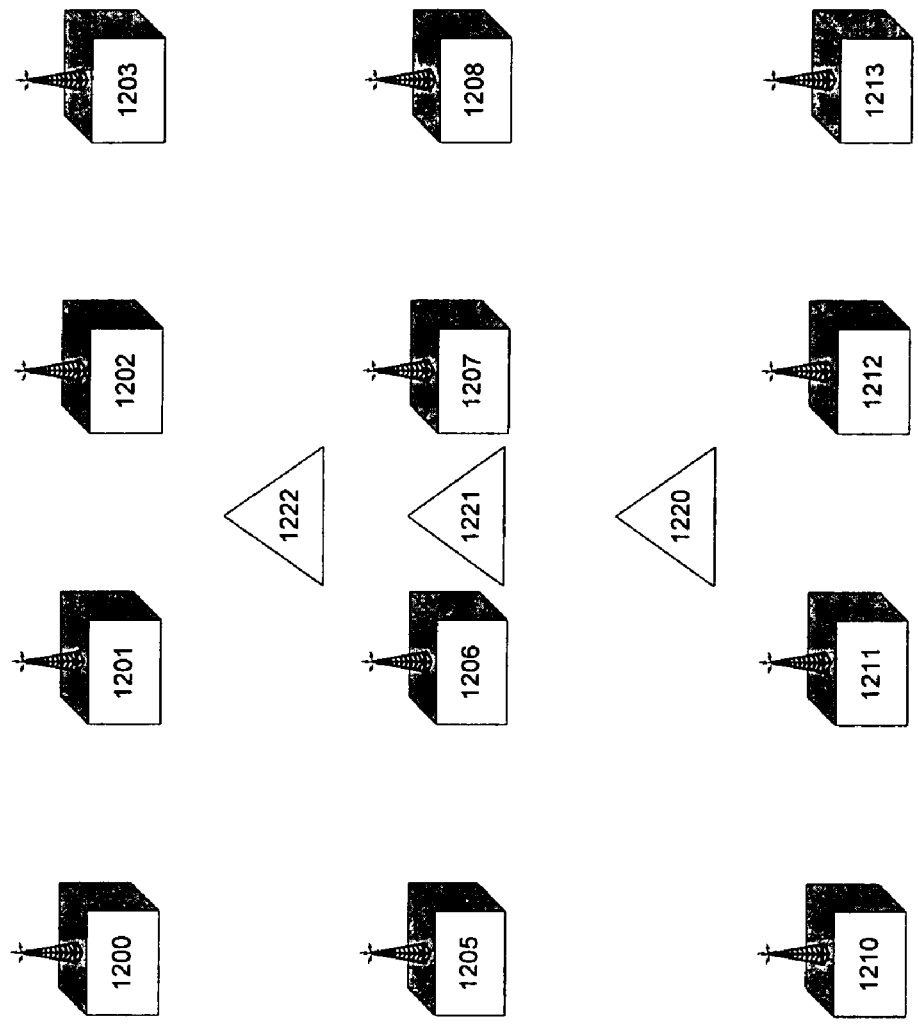

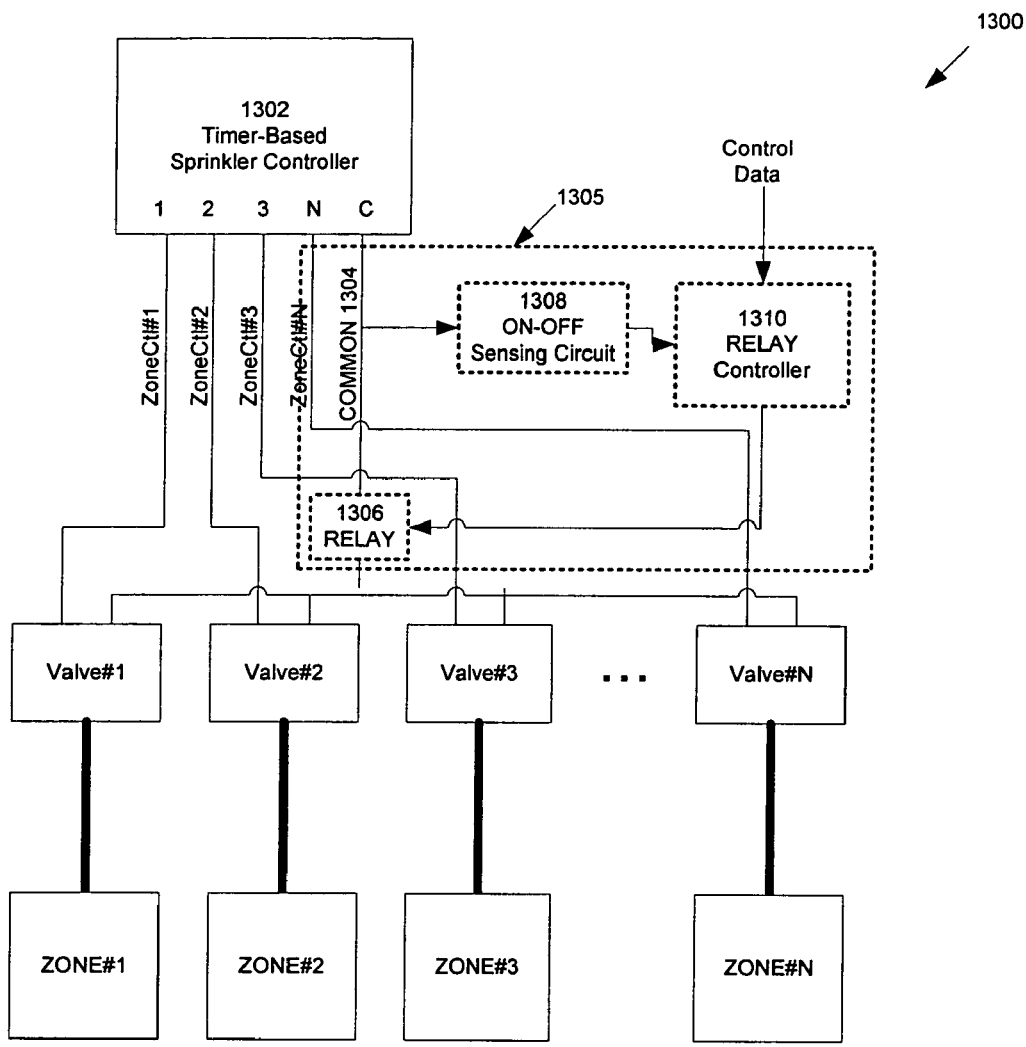
Figure 13 - Common Line Control
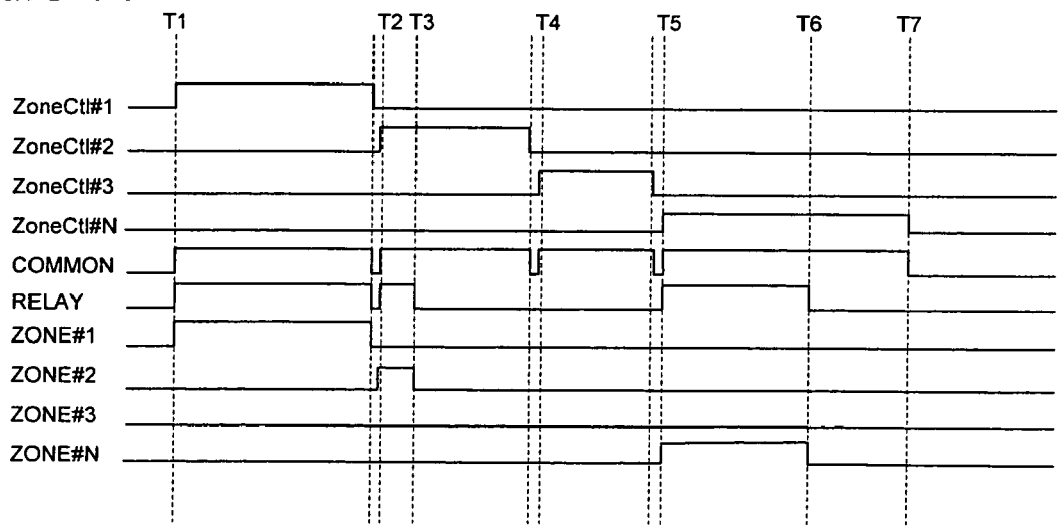
Figure 14

WIRELESS SENSOR PROBE

CROSS REFERENCE TO RELATED APPLICATION

This application claims the benefit of U.S. Provisional Patent Application Ser. No. 60/421,963, filed Oct. 28, 2002, entitled "System for Environmental Monitoring and Control," of Dale K. Hitt, which application is incorporated herein by reference in its entirety.

This application is related to the following concurrently filed and commonly assigned U.S. patent applications: U.S. patent application Ser. No. 10/692,532 filed Oct. 24, 2003, entitled "Wireless Sensor System for Environmental Monitoring And Control," of Dale K. Hitt; U.S. patent application Ser. No. 10/692,476 filed Oct. 24, 2003, entitled "Distributed Environmental Control In A Wireless Sensor System," of Dale K. Hitt; U.S. patent application Ser. No. 10/692,518 filed Oct. 24, 2003, entitled "Scheduled Transmission In A Wireless Sensor System," of Dale K. Hitt, now U.S. Pat. No. 7,339,957 issued Mar. 4, 2008; U.S. patent application Ser. No. 10/692,519 filed Oct. 24, 2003, entitled "RF Based Positioning and Intrusion Detection Using A Wireless Sensor Network," of Dale K. Hitt; and U.S. patent application Ser. No. 10/692,645 filed Oct. 24, 2003, entitled "Two-Wire Control of Sprinkler System," of Dale K. Hitt et al. The aforementioned patent and patent applications are incorporated herein by reference in their entireties.

FIELD OF THE INVENTION

The invention relates to a wireless sensor system for environmental monitoring and/or control and, in particular, to systems and methods for an improved environmental monitoring and control system utilizing distributed wireless sensor platforms to provide continuous samples from multiple sensor types and multiple sensor positions and to establish multiple control points without the need for a centralized control.

DESCRIPTION OF THE RELATED ART

Control systems for automatic irrigation systems used for landscape and agricultural maintenance are known. Most common types of environmental monitoring and control for irrigation systems incorporate a means of controlling the start time and duration of watering cycles via a central timing controller. The need to adjust a watering cycle due to the environmental influence is necessary in order to save natural resources, reduce costs, and to improve the growing environment for plants. Such environmental conditions include temperature changes, relative humidity, precipitation, wind and cloud cover. In conventional control system, the primary means for halting an automatic watering cycle when certain environmental event occurs is by an operator manually suspending the cycle at the irrigation controller. In most situations this proves to be an ineffective means of conserving resources due to the inconsistent and inefficient methods followed by the operator. In fact, quite often the operator ignores the need to suspend the watering cycle altogether, and in some cases neglects to resume the watering cycle when required, leading to both over-watered and under-watered landscaping.

It is because of this unreliable and inconvenient manual method that environmental sensors were developed that allow for an automatic interruption of the controller due to an environmental condition. The use of sensors for irrigation systems has proven to be an effective and economical method of conserving water, energy, and money.

One of the major drawbacks of the conventional environmental sensors is the extensive installation time and difficult methods required for a proper installation. A soil moisture sensor is usually installed in the ground by boring of an precisely sized hole, placing the sensor at the appropriate depth to measure the soil properties in the root zone, placing a slurry of water and soil in the hole to assure that the sensor has good contact with the soil and try to restore the soil in the hole to its' previous condition as much as possible so that the sensor provides readings that correctly reflect the state of the soil. If the soil is not restored properly, water and fertilizer can drain down along the hole to the sensor and corrupt the sensor readings.

It is common for soil to be stratified into regions of varying textures, composition and drainage properties. Digging a hole and refilling it with slurry disrupts these strata around the sensor and decreases the accuracy of the sensor readings.

As the soil cycles from wet to dry, it is possible to shrink back from the senor and loose contact. If this happens, the sensor can no longer read the soil status properly. Sometimes, rewetting the soil is not sufficient to restore the sensor contact and the sensor must be reinstalled.

The wires that run from the sensors up through the soil to the surface are then routed either to a central controller directly or to a central controller through a wireless transmission system. This method is burdensome in time, tools required and is prone to unsuccessful installation through poor seating of the sensor in the soil, poor representation of the target soil by the sensed soil that was disturbed by installation, and electrical noise in connecting wires. The central controller receives the signals from the remote sensors and determines whether or not to start the next irrigation cycle for a particular irrigation zone.

By way of example, conventional sensors and sensor controlled irrigation systems are described in U.S. Pat. No. 5,424,649 to Gluck et al.; U.S. Pat. No. 5,351,437 to Lishman; U.S. Pat. No. 4,937,732 to Brandisini; U.S. Pat. No. 5,083,886 to Whitman; U.S. Pat. No. 4,524,913 to Bron; and U.S. Pat. No. 4,971,248 to Marino; and U.S. Pat No 5,813,606 to Ziff. FIG. 1 duplicates FIG. 1 of the Ziff patent and illustrate a radio controlled sprinkler control system where a transmitter including a moisture sensor communicates with a receiver controlling the actuation of the sprinklers. The sprinklers are actuated by a signal generated by the moisture sensor disposed to measure the moisture level of the ground.

The cultivation of agricultural crops has evolved over the years as the size and scale of farms has increased from small family farms to large-scale farms. Irrespective of a farm's size, variations in terrain, soil conditions and weather exposure produce non-uniformities of field conditions which affect the preparation and growing of crops. In order to optimize crop yields, farmers have historically kept track of rainfall, humidity and temperature, as well as soil conditions and the occurrence of pest infestations. Soil has been analyzed to determine nitrogen levels and various other conditions. Furthermore, advances have been made with the introduction of field condition sensing and data collection that enable gross categorization of agronomic information on a field. However, further improvements are needed that will enable better collection and management of information so that yields can be increased, without increasing the costs of production.

Recently, in-ground moisture sensors have been combined with an irrigation controller to control an irrigation cycle of an area of soil. More particularly, such irrigation controllers have been used to control stationary irrigation devices such as those used in golf courses and in orchards. However, such systems were limited in that in-ground sensors have required costly long range wireless communications systems to send data back to a central monitoring and control unit. Therefore, it is cost prohibitive to provide a large number of sensors in order to cover a large agricultural field being processed by a large-scale irrigation device such as a center-pivot irrigation device. Furthermore, such stationary irrigation systems are not suitable for irrigating large-scale agricultural fields due to the large number of sprinklers needed on the irrigation system. Furthermore, an agricultural field needs to be periodically cultivated and a complex in-ground irrigation system will cause problems when the field is being turned over and prepared for its next cultivation cycle.

Other areas of recent improvement in the field of agriculture involve the use of precision agriculture products. Precision agriculture products typically utilize variable-rate application devices, global positioning system (GPS) devices, and geographic information systems (GIS). Satellite-based global positioning systems enable the determination of precise locations within a field of interest. Geographic information systems enable data management of detected conditions on a field of interest.

One presently available representative differential global positioning system is manufactured by Trimble, and is sold under the product name Direct GPS for Arc View, Trimble Surveying and Mapping Division, 645 North Mary Avenue, P.O. Box 3642, Sunnyvale, Calif. 94088-3642.

One representative geographic information system (GIS) is presently available from Environmental System Research Institute, Inc. (ESRI), 380 New York Street, Redlands, Calif. 92373-8100, under the name "ARCVIEW.RTM for Agriculture." Such a GIS system enables the management of agricultural information by way of a graphical user interface. The GIS system consists of software implemented on a computer, and forms a graphical display that easily enables a user to tabulate data and evaluate collected data for making decisions about a crop being cultivated.

Far-distance data collection techniques have been used for determining certain agronomic features on a field being studied. Satellites imaging techniques and aerial photography techniques have enabled the collection of vast arrays of data in order to characterize agronomic information on large fields of interest. For example, thermal imaging cameras have been used to determine thermal characteristics of a field being observed. However, such cameras produce an array of pixels having limited resolution, and further, the cameras can only collect information periodically when weather conditions permit flight overhead. The presence of certain crop and soil conditions can manifest themselves in the form of a thermally detectable variation upon the land. Detection can also be performed in the visible, infrared and ultraviolet ranges, enabling the determination of correlated features with such information.

However, the ability to collect agronomic information on a field of interest via far-distance imaging techniques often has limited capabilities. For example, inclement weather conditions can block the ability to detect agronomic features. For cases of satellites, the presence of cloud cover can disrupt detection of such information. During certain periods of a growing cycle for a crop, the timing of such information can be critical to successful harvesting. The data from these techniques is not available continuously, therefore is inappropriate for providing real-time feedback for control of irrigation systems. Hence, an improved technique that enables the continuous detection of such agronomic information during any time of day, and under any type of weather condition, is desired. Furthermore, a sensing device that enables the detection of an increased number of different agronomic features is also desired. Even Furthermore, sensing devices that enable closed-loop control of irrigation is required.

Although precision agriculture products have recently enhanced the ability to increase crop yields, further improvements are needed to reduce the overall cost and usability of such systems while improving the effectiveness. For example, improvements are needed to sensor based, closed-loop control of such systems to better control the application of water and/or chemicals to a field based upon the real-time detection of needs. Furthermore, improvements are needed to the sensing systems in order to reduce their overall cost, while enhancing their effectiveness.

There are a variety of systems for monitoring and/or controlling any of a number of systems and/or processes, such as, for example, manufacturing processes, irrigation systems, personal security systems, and residential systems to name a few. In many of these systems, a central host computer in communication with a wide area network monitors and/or controls a plurality of remote devices arranged within a geographical region. The plurality of remote devices typically uses remote sensors to monitor and actuators to respond to various system parameters to reach desired results. A number of automated monitoring systems use computers or dedicated microprocessors in association with appropriate software to process system inputs, model system responses, and control actuators to implement corrections within a system. In control systems, the dependence on a central controller reduces the reliability of the system because a failure in this controller brings down the system.

Various schemes have been proposed to facilitate communication between the host computer and the remote devices within the system, including RF transmission, and control signal modulation over the local power distribution network. For example, U.S. Pat. No. 4,697,166 describes a power-line carrier backbone for inter-element communications. As recognized in U.S. Pat. No. 5,471,190, there is a growing interest in home automation systems and products that facilitate such systems. Recognizing that consumers will soon demand interoperability between household systems, appliances, and computers, the Electronics Industry Association (EIA) has adopted a standard, known as the Consumer Electronics Bus (CEBus). The CEBus is designed to provide reliable communications between residential devices.

One problem with the use of control systems technology to distributed systems is the cost associated with developing the local communications infrastructure necessary to interconnect the various devices. A typical approach to implementing control system is to install a local network of hard-wired sensors and actuators along with a local controller. Not only is there expense associated with developing and installing appropriate sensors and actuators, but the expense of connecting functional sensors and actuators with the local controller is often prohibitive. Another prohibitive cost is the expense associated with the expense associated with programming the local controller.

Accordingly, an alternative solution for implementing a distributed control system suitable for monitoring and controlling remote devices that overcomes the shortcomings of the prior art is desired.

U.S. Pat. No. 5,905,442 discloses a wireless automation system with a centralized remote control that controls I/O devices for providing electrical power to appliances from power outlets of the power mains in building. The remote control and I/O devices comprise RF transceivers, and the system includes dedicated repeater units for repeating signals to I/O devices out of the range of the remote control.

U.S. Pat. No. 5,875,179 describes a method for synchronizing communications over a backbone architecture in a wireless network. The system invokes two controllers, one of which is a master and another which is an alternate master which will be activated only when the master is out of work. Dedicated repeaters and I/O devices in the system are commonly designated as nodes. There are generally functional difference between repeater nodes and end (I/O) nodes.

U.S. Pat. No. 4,427,968 discloses a wireless automation system with flexible message routing. A central station produces a signal for a I/O device; the signal contains a route code, an address code, an identifying code and a message code. Dedicated repeaters in the architecture receive the signals and follow a specified procedure for repeating signal. Repeaters may also be addressed as end nodes, e.g. in order for the controller to download routing tables.

U.S. Pat. No. 4,250,489 describes a communication system having dedicated repeaters organized in a pyramidal configuration. The repeaters are bidirectionally addressable and may receive interrogation signals telling a repeater that it is the last repeater in the chain. The repeaters are not connected to appliances and do not perform any functions besides repeating and routing signals.

SUMMARY OF THE INVENTION

According to one embodiment of the present invention, a wireless sensor probe for use in environmental monitoring and control includes a separable probe body and sensor mast. The probe body includes a void configured to house the sensor mast including one or more sensor devices for sensing a soil property surrounding the probe body when the probe body is inserted partially into the ground. The probe body includes a probe top part for encapsulating the probe body and the sensor mast. The sensor mast is inserted into the probe body to form the sensor probe. In another embodiment, a wireless sensor probe includes a housing containing one or more sensor devices. The probe further includes a collar situated near a top portion of the housing being used to anchor the housing to the top of the ground and a gasket formed on the outside perimeter of the housing for securing the housing in the ground.

The present invention is better understood upon consideration of the detailed description below and the accompanying drawings.

BRIEF DESCRIPTION OF THE DRAWINGS

FIG. 2A, is a schematic diagram of a wireless environmental monitoring and control system according to one embodiment of the present invention.

FIGS. 10A and 10B illustrate differential embodiments of the sensor nodes of the present invention.

FIG. 11 illustrates variations on the probe body configuration.

FIG. 12 is a schematic diagram illustrating the use of the environmental monitoring and control system of the present invention for occupancy detection.

FIG. 13 is a block diagram of an automatic sprinkler system 1300 incorporating the two-wire control system according to one embodiment of the present invention.

FIG. 14 is a timing diagram illustrating the operation of the sprinkler system of FIG. 13 according to one embodiment of the present invention.

DETAILED DESCRIPTION OF THE PREFERRED EMBODIMENTS

In accordance with the principles of the present invention, a wireless environmental monitoring and control system utilizes an array of wireless sensors for providing extended range and multiple control points within the array. The wireless environmental monitoring and control system can support sensing and irrigation control over a large area without the need for a central controller. By providing distributed monitoring and control, the control system of the present invention can be used to realize more efficient water utilization and improved crop yield.

A. Multi-hop Wireless Sensor Irrigation Control System

Figure 1:
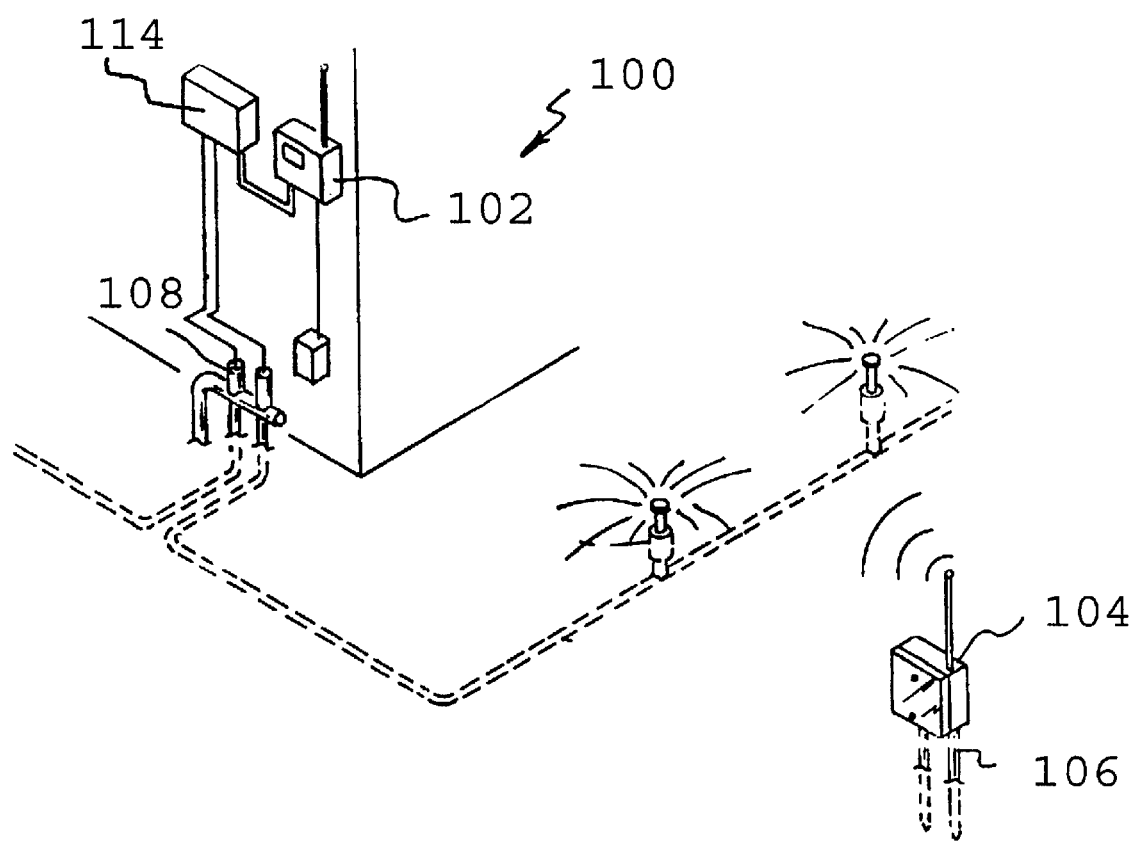
FIG. 1 is a radio controlled sprinkler control system as described in U.S. Pat. No. 5,813,606.
Figure 2:
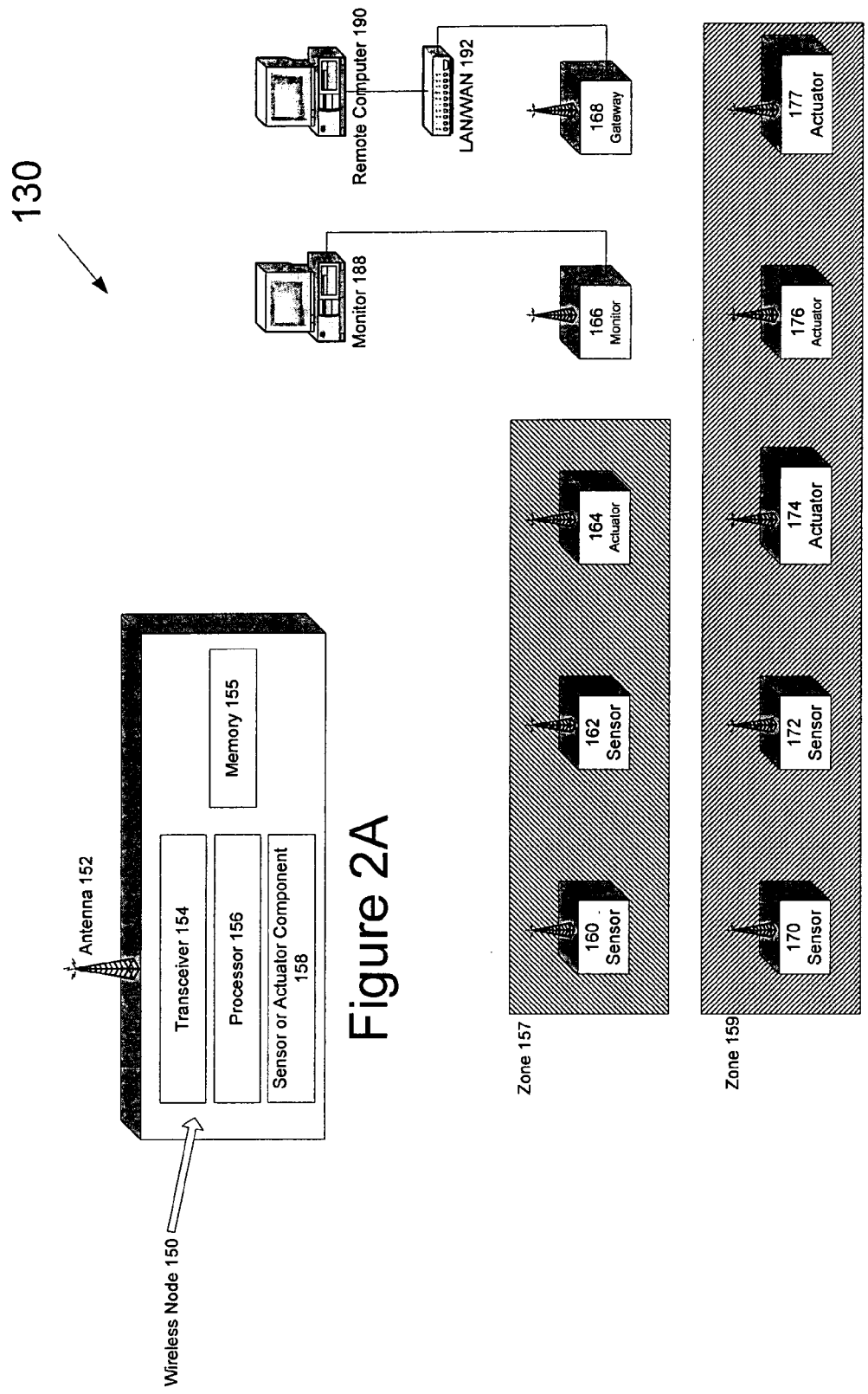
FIG. 2, including insert

FIG. 2 is a schematic diagram of a wireless environmental monitoring and control system according to one embodiment of the present invention. In general, wireless environmental monitoring and control system 130 (system 130) is configured to include one or more irrigation zones where each irrigation zone can include one or more sensor nodes and one or more actuator nodes. System 130 can also include other nodes providing other supporting functions as will be described in more detail below. The sensor nodes, actuator nodes and other nodes in system 130 form a wireless communication network in which messages, such as sensor data, operating data, and commands, are communicated wirelessly between the nodes.

In FIG. 2, wireless environmental monitoring and control system 130 (system 130) is illustrated with irrigation zones 157 and 159. In the present embodiment, irrigation zone 157 is supported by sensor nodes 160 and 162 and an actuator node 164. Actuator node 164 controls one or more irrigation valves for providing irrigation within zone 157. Sensor nodes 160 and 162 can represent different types of sensors for providing sensor data or commands to actuator 164 to control the irrigation of zone 157. Actuator 164 is thus disposed to receive sensor data or commands from one or more sensor nodes. Irrigation zone 159 is supported by sensor nodes 170 and 172, actuator nodes 174 and 176 and a repeater node 177. Actuator nodes 174 and 176 each control one or more irrigation valves for providing irrigation within zone 159. Similar to zone 157, sensor nodes 170 and 172 can represent different type of sensors and can transmit sensor data or commands to multiple actuator nodes 174 and 176. Each of actuator nodes 174 and 176 can receive sensor data or commands from one or more sensor nodes.

Wireless environmental monitoring and control system 130 can also include other nodes for providing other supporting functions. Referring to FIG. 2, the sensor and actuator nodes within system 130 also communicate with nodes with monitoring capabilities only. For example, a local monitor node 166 is provided for communication with any one of the sensor and actuator nodes. Local monitor node 166 can be coupled to a personal computer 188 for receiving, storing and/or processing data received from the sensor nodes or actuator nodes. A gateway node 168 can also be provided to facilitate access to a local area network or the internet. In the present embodiment, gateway node 168 is connected through a local area network to a computer 190 which provides access to the Internet or an intranet. In this manner, monitoring and/or control of system 130 can be facilitated remotely through a local area network through the Internet. A repeater node 177 is also provided. Repeater node 177 does not provide other functions and act only to relay messages between the nodes in system 130. In one embodiment, a sensor node or an actuator node can also act as a repeater node for relaying messages between other nodes. System 130 can also include a user interface node (not shown) whereby a user can access the network of sensor and actuator nodes for reading data and for providing control.

In system 130, each sensor node and each actuator node incorporates a wireless communication transceiver to enable wireless communication between the nodes. An insert FIG. 2A in FIG. 2 is a block diagram of a sensor/actuator node according to one embodiment of the present invention. In the present description, a sensor node, an actuator node or other nodes in the system will be collectively referred to as "a wireless node" in the environmental monitoring and control system of the present invention. In FIG. 2A, a wireless node 150 includes an antenna 152, a wireless transceiver 154, a processor 156 and a node component 158. The wireless transceiver of each wireless node may communicate with a memory 155 that stores a unique transceiver identifier that identifies the wireless network. Depending on the function of the wireless node, the node component may further include sensor or actuator components. For example, if wireless node 150 is a sensor node, node component 158 will be implemented as a sensor component, such as a soil moisture sensor or an temperature sensor. If wireless node 150 is an actuator node, node component 158 will be implemented as an actuator component for providing the drive voltage to drive one or more irrigation valves.

Each wireless node in system 130 can be powered by a power source, such as by solar power or by battery power. In one embodiment, the wireless node is powered by a rechargeable battery. The rechargeable battery may be recharged periodically via a solar panel. In one embodiment, the transceiver circuit is independently powered so that when the wireless node is acting merely as a repeater for relaying transmissions to other wireless, the transceiver does not drain power away from the sensor or the actuator component. In one embodiment, the battery power level or the solar power level at each wireless node is measured and monitored so that power failures at any node can be detected.

Processor 156 controls the operation of the wireless transceiver and the node component. Processor 156 usually includes a data interface configured to receive and/or transmit signals to node component 158. If the signal output from the sensors/actuator components is an analog signal, the data interface may include an analog-to-digital converter (not shown) to digitize the signals. For example, processor 156 can be operated to receive incoming control data from transceiver 154 and use the control data to control the actuator component. Processor 156 can also be operated to receive sensor data from a sensor component and direct the sensor data to be transmitted to an actuator node through the transceiver. Processor 156 can also be provided with programming data to derive control data for an actuator node based on the sensor data received.

In accordance with the present invention, the wireless node can be built using different degrees of the integration. In one embodiment, the transceiver circuit, the processor and the memory are integrated in the same housing as the sensor or actuator component. In another embodiment, the transceiver circuit may be installed in close proximity to the processor and sensor/actuator components and communicate with the processor via a wired or a wireless connection.

In one embodiment, the sensor component can be any one of or a combination of: an air temperature sensor, a relative humidity sensor, a light level sensor, a soil moisture sensor, a soil temperature sensor, a soil dissolved oxygen sensor, a soil pH sensor, a soil conductivity sensor, a soil dielectric frequency response sensor. The actuator component can be any one of or a combination of: an actuator position control, an actuator flow rate control, a water flow control, a fertilizer flow control, and a lighting control.

In one embodiment, each of the wireless nodes in environmental monitoring and control system 130 is configured to transmit a low-power radio frequency (RF) signal. Thus, each wireless node requires limited power to operate. The transmitter power and range may be appropriately selected for the desired operating requirements. More specifically, in one embodiment, each sensor or actuator node operates as a repeater node for relaying control or sensor data to other nodes within the system, thereby effectively extending the range of each node, as will be described in more detail below.

In FIG. 2, the wireless nodes are depicted without a user interface. However, in other embodiments, the wireless nodes may be equipped with a user interface, including but not limited to pushbuttons, switches, an alphanumeric keypad, LED indicators, LCD display or any other type of user interface device suitably configured with software to accept operator input. Wireless nodes that require user input, but do not have user interfaces can receive user input from nodes that do have user interfaces.

B. Distributed Environmental Control

In accordance with the present invention, the irrigation control actuator does not need to be controlled from a central controller. The actuator node can receive sensor data or commands directly over the system and determine the appropriate control response from the sensor data. The actuator node can coordinate with other actuator nodes in the network to sequence through irrigation cycles so that water pressure is maintained. As is well understood in the art, if too many sprinklers are on at once, water pressure can be reduced below necessary levels.

With an interconnected wireless network such as system 120 that provides processing capabilities at every node, nodes on the network can distribute signal processing, storage and analysis function to better optimize the use of the network resources. A distributed environmental control system for efficient and effective system management is thus realized. By providing a distributed control, the operation of wireless environmental monitoring and control system 130 can be flexible and various fail-safe can be realized.

In one embodiment, the sensor nodes collect sensor data and determine actuator function as needed. When actuator function is needed, messages can be sent across the wireless network from a sensor node to the respective actuator node. In another embodiment, any wireless node in the network can integrate data from one or more sensor nodes to determine the appropriate actuator function. Such a wireless node is sometimes referred to as "an intermediate node" where sensor data are sent for processing and resulting actuator commands are forwarded to the respective actuator nodes. The intermediate node functions as a data processing station supporting respective sensor nodes and respective actuator nodes.

In another embodiment, every wireless node in the network can receive data or commands from other wireless nodes, including user input nodes, actuator nodes, sensor nodes and other monitor nodes (like gateway nodes). Each wireless node integrates those data and/or commands to determine the correct operations. In one embodiment, sensor data from the sensor nodes are broadcast to all nodes in the network. Actuator nodes receiving the sensor data can selectively process the sensor data relevant to their function. For example, an actuator node in irrigation zone1 receives data and processes the data from all sensor nodes related to the zone1 only. The actuator node can also receive sensor data from weather sensor nodes and user input nodes and gateway nodes to have more information to make actuator decisions.

In system 130, any of the wireless node, whether it is a sensor node or an actuator node, can transmit messages to any other node. Thus, a sensor node can process sensor data it is sensing and can issue commands to an actuator node for controlling the irrigation of a zone. Alternately, a sensor node can collect sensor data from itself and sensor data from other sensor nodes in the respective area and process the sensor data collectively. The sensor node can then provide commands accordingly to control the operation of the associated actuator node 164.

In one embodiment, an actuator node sends a message to an associated sensor node requesting sensor data and/or commands. The sensor node in response processes the sensor data from itself or from associated sensor nodes and provide the sensor data and/or actuator commands to the requesting actuator node.

As described above, any wireless node in the network can function as a repeater node where messages are relayed or a data processing station where sensor data are processed and commands are generated. Thus, a wireless node wishing to transmit to another wireless node can utilize one or more intermediate repeater nodes for transmitting the message.

Figure 3:
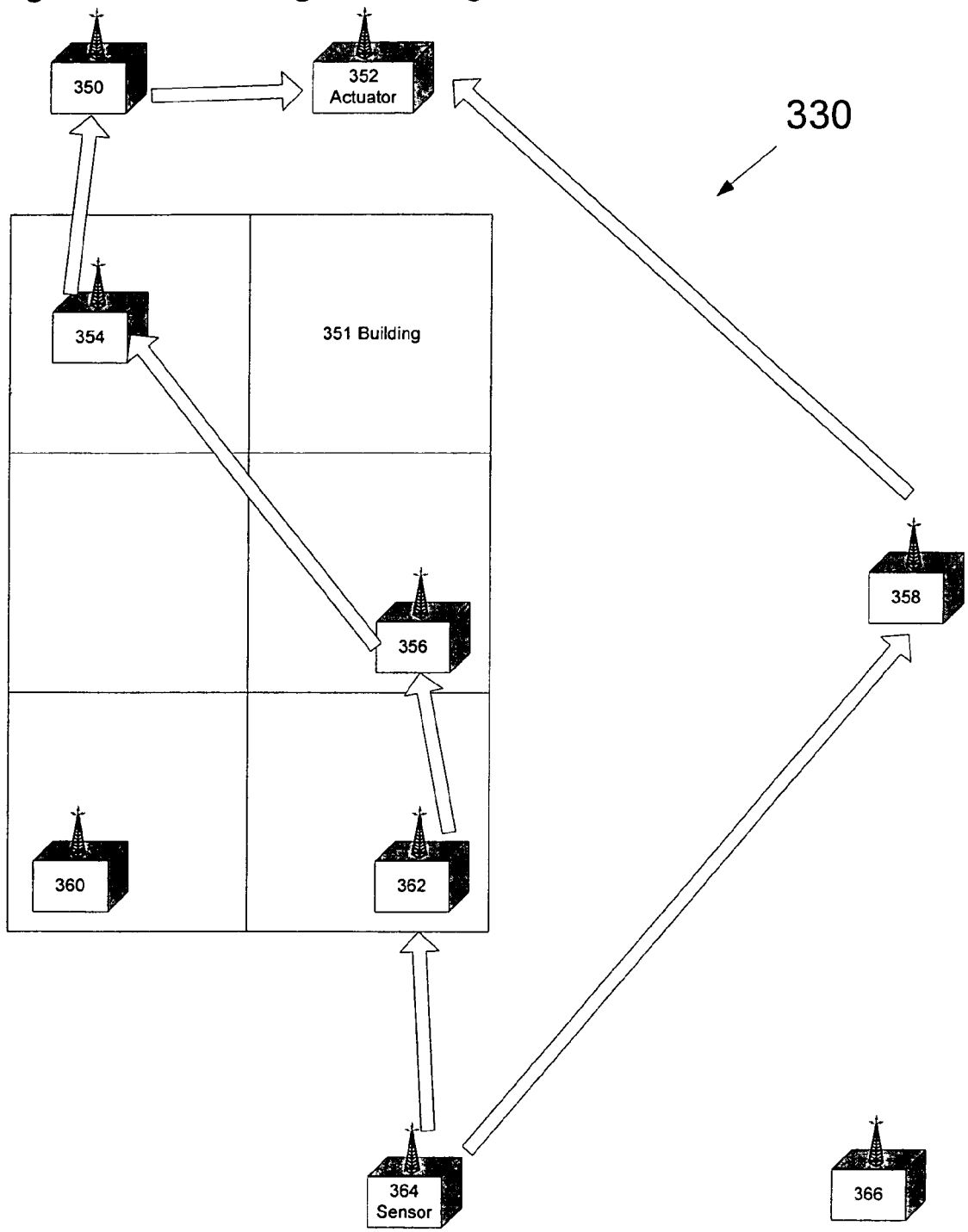
FIG. 3 is a block diagram illustrating the operation of a wireless environmental monitoring and control system according to one embodiment of the present invention.

Referring to FIG. 3, sensor node 160 may communicate with at least one actuator node 164 either directly or via another wireless node, such as sensor node 162. Similarly, sensor node 170 may communicate with at least one or more other sensor/actuator nodes, such as node 176, on the network via wireless node 172. Furthermore, one or more sensor/actuator nodes may be in direct communication with one or more monitor nodes 166 and 168. In an alternate embodiment, the communication medium between the one or more sensor/actuator nodes may be wireless or, for relatively closely located configurations, a wired communication medium may be used.

One or more wireless nodes are configured and disposed to receive remote data transmissions from the various standalone wireless nodes. It is important to note that while a specific group of wireless nodes is assigned to a given zone, all of the wireless nodes within the environmental monitoring and control system can communication with each other to relay messages to the desired node. For example, sensor node 160 in zone 157 can transmit a message to actuator node 164 through sensor node 172 in zone 159, if that route is determined to be better suited for transmission. Similarly, sensor node 170 in zone 159 can transmit sensor data to actuator node 176 through sensor node 162 and actuator node 164, if that route is determine to be better suited for transmission.

Similarly, any of the wireless nodes in the system can communicate with the monitor node and the gateway node. Wireless gateway node 168 may be configured to convert the transmissions between TCP/IP format and wireless network format to provide communications between devices on the wireless network and remote device 190 via TCP/IP.

FIG. 3 is a block diagram illustrating the operation of a wireless environmental monitoring and control system according to one embodiment of the present invention. In FIG. 3, wireless nodes 350-366 in environmental monitoring and control system 330 are geographically arranged such that the antenna patterns (not shown) associated with each wireless node overlap to create a coverage area. In this manner, environmental monitoring and control system 330 enables a wireless network node 364 (a sensor node) associated with the coverage area to communicate with another wireless node 352 (an actuator node) in the coverage area via several possible communication paths. For instance, wireless node 364 may communicate with wireless node 352 via several different communication paths, each path defined by one or more wireless nodes within the coverage area. For example, in FIG. 3, sensor node 364 may communicate with actuator node 352 via a wireless node 358 which can be a sensor node, an actuator node, or a monitoring node. Alternately, sensor node 364 may communicate with actuator node 352 through a series of intermediate nodes 362, 356, 354 and 350. In this manner, the range of each wireless node can remain small to limit power consumption while ensuring a wide coverage area for system 300.

Figure 4:
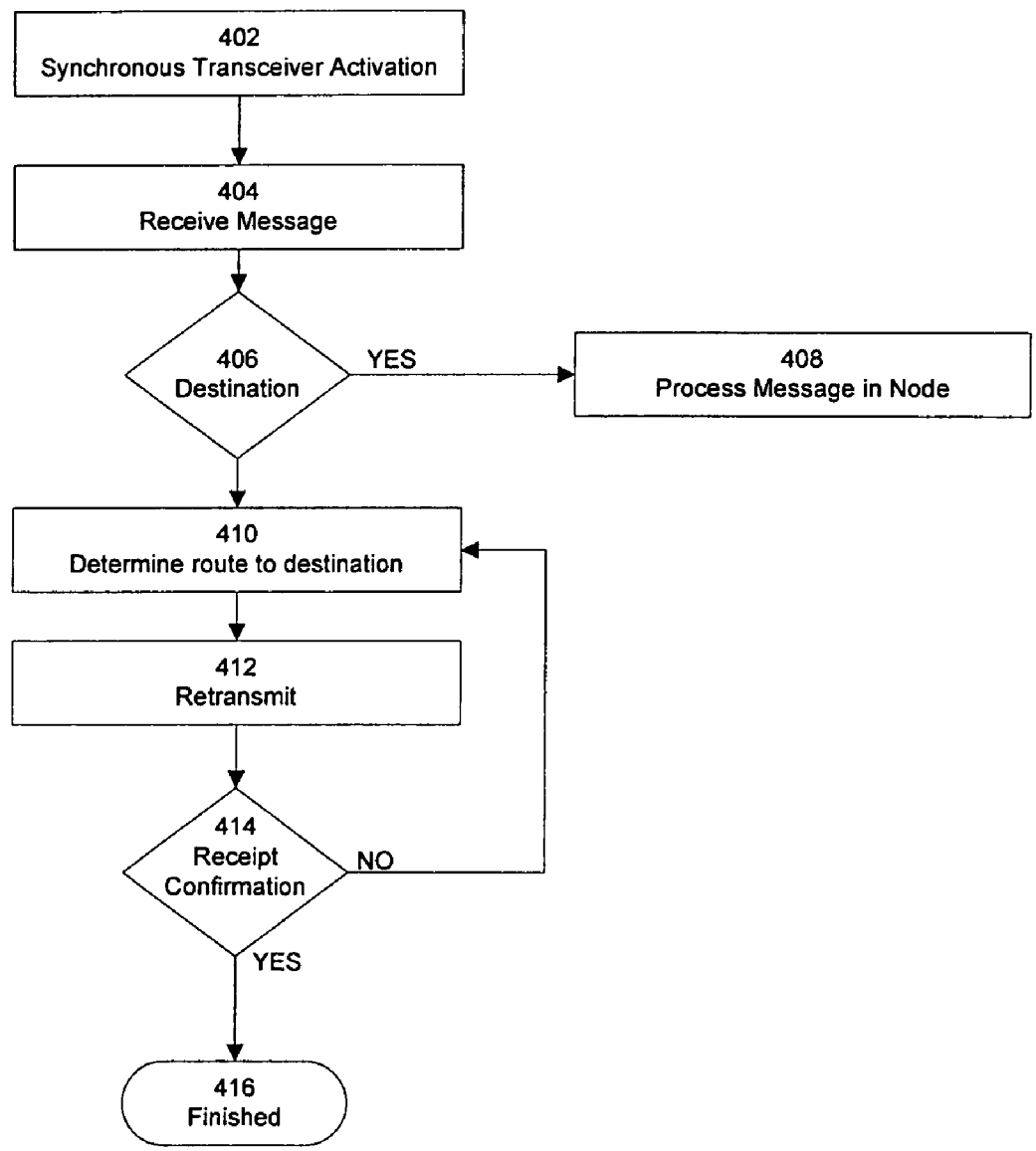
FIG. 4 is a flow chart illustrating the operation of each wireless node for receiving and transmitting messages within the environmental monitoring and control system according to one embodiment of the present invention.

FIG. 4 is a flow chart illustrating the operation of each wireless node for receiving and transmitting messages within the environmental monitoring and control system according to one embodiment of the present invention. In the present embodiment, the transceivers in the wireless nodes of the system are synchronously activated to establish end-to-end network connectivity (step 402). The wireless transceiver receives an incoming message via the antenna (step 404). The transceiver receives the incoming message, modifies the received signal, and passes the modified signal onto the processor. The processor evaluates the message to determine the intended recipient (step 406). If the intended recipient is the wireless node itself, the processor then prepares the appropriate response (step 408). The response may include collecting data from the sensor or providing a control signal to the actuator. If the intended recipient is not the wireless node itself, the processor then prepares the message to be re-transmitted to the intended recipient. Specifically, the processor of the wireless node determines the best route to the destination (step 410) and retransmits the message as necessary (step 412). The best route can be determined by the smallest number of intermediate nodes, by nodes with the maximum power available and by most reliable links. The wireless node awaits confirmation of receipt of the message (step 414). When the confirmation is not received, the wireless node attempts to retransmit the message by returning to step 410. When confirmation is received, the processing for the message is completed.

The logic circuits for supporting the operation of each wireless node can be implemented in software or in firmware that is stored in a memory, such as memory 155. The processor of the wireless node executes the instructions stored in the memory to carry out the message interpretation and transmission functions.

In one embodiment, the operation of environmental monitoring and control system for transmitting sensor data and control data can be implemented as follows. First, the transceiver in a wireless node may receive a command message on the antenna via a message protocol. The command message may be initiated from another wireless node, or any other device connected to the system through a gateway. The processor may evaluate the received message to determine if the recipient's address is its own unique address. If it is, then the processor evaluates the command and prepares a response message.

In response to the command message, the processor receives the data related to the sensor or the actuator. In one embodiment, the data may be retrieved by initiating a request to the sensor or actuator. In another embodiment, the data may be stored in the memory and the processor retrieves the data from the memory 208. The processor may also retrieve the unique address locations of the data from the memory. Then, the processor formats a transmit signal in response to the command message as described above. The processor then communicates the transmit signal to the transceiver, which provides the transmit signal to the wireless control system. The transmit signal is then delivered to the intended point, such as a monitoring node.

Figure 5:
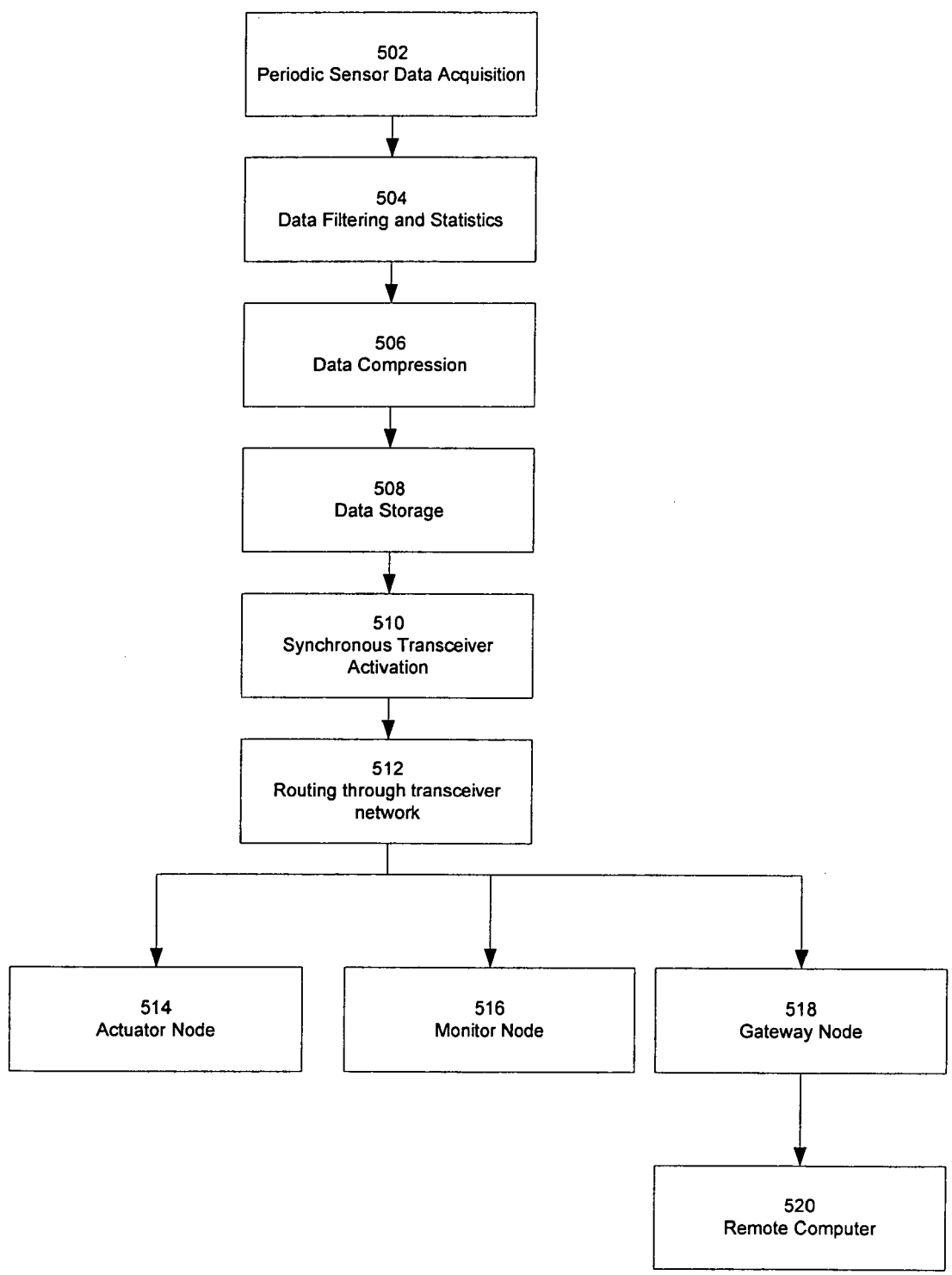
FIG. 5 is a flow chart illustrating the sensor data processing and routing operation according to one embodiment of the present invention.

According to an alternate embodiment of the present invention, a sensor node can periodically sample the sensor and the sensor data is aggregated into a local memory for processing and/or transmission. FIG. 5 is a flow chart illustrating the sensor data processing and routing operation according to one embodiment of the present invention. Referring to FIG. 5, the sensor node is programmed to periodically acquire sensor data (step 502). Then, the sensor data is filtered (step 504) and/or compressed and/or processed (step 506). Data compression may be performed to reduce the data transmission requirements and improve the usability of the data by other nodes in the network. Noise filtering can include noise reduction, cross-channel interference reduction, missing sample interpolation and other signal processing to enhance the quality of the data. Compression can include differential coding within a channel or jointly between multiple correlated channels. Processing can include statistical analysis (average, median, standard deviation and higher order correlations), linear regression, linear approximation and other mathematical modeling processes to improve the usability of the data. The processed sensor data is stored in a local memory (step 508).

The processed sensor data can then be delivered to other wireless nodes in the system as created on a periodic schedule or as requested by other nodes in the system. If the data is delivered as created, or on a periodic schedule, the wireless node should have stored the address of the target network nodes that need to receive the data. If the data is delivered on a periodic basis, the schedule for delivery to a target network node should be stored. If data is delivered as requested, or on command from another node in the network, the request or command contains the address of the requester to where the data is to be sent.

At step 510, synchronous transceiver activation is performed to activate all wireless nodes within the system or within a zone in a system. Then, the sensor data is routed through the network of wireless nodes to the intended recipient, such as the actuator nodes (step 514), a monitor node (step 516), and a gateway node (step 518). The gateway node may forward the message to a remote computer (step 520). In the case where the sensor data is transmitted to an actuator node, the sensor data is used to control the state of the actuator.

A distinct difference between the conventional irrigation control system and the control system of the present invention is that no central control unit is required for the operation of the actuators and sensors. In accordance with the present invention, all coordination between actuators, sensors, and other operation points, such as gateways, monitor points user interface point, or user input point, is accomplished across the system through distributed control and without the need for a central controller.

Figure 6:
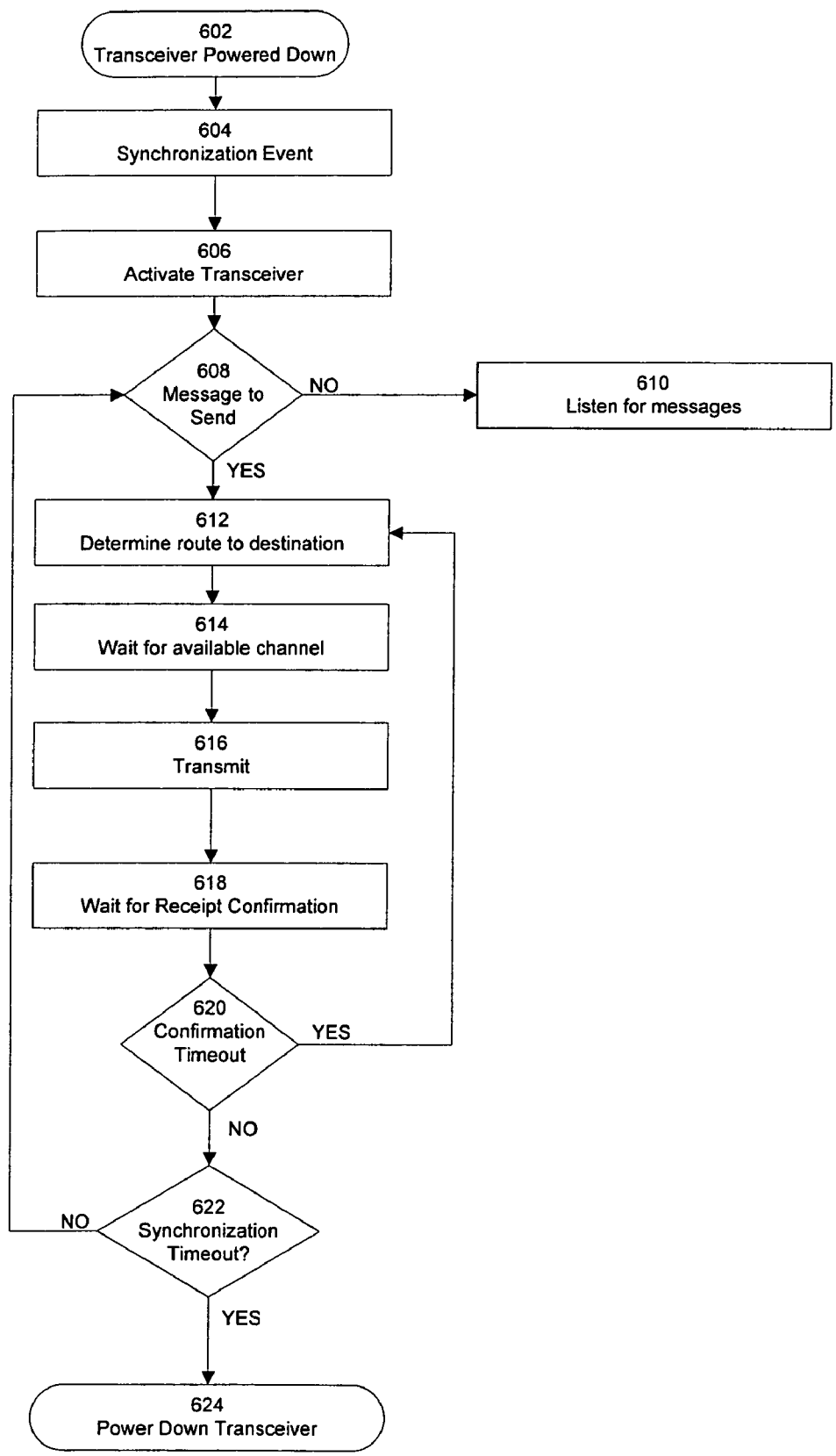
FIG. 6 is a flow chart illustrating the transceiver synchronization operation according to one embodiment of the present invention.

When the wireless nodes are powered by battery power or solar power, power conservation is important. To conserve power, the transceivers in the wireless nodes can remain powered down. However, to restore end-to-end network connectivity, the nodes must all be active so that messages can be forwarded through the nodes. FIG. 6 is a flow chart illustrating the transceiver synchronization operation according to one embodiment of the present invention. Referring to FIG. 6, in normal operation, the environmental monitoring and control system causes the transceivers of all the wireless nodes to power down (step 602). Then, when messages are to be transmitted, a synchronization event is used to synchronously bring all nodes out of a powered down state (step 604). The synchronization event can be time based, such as a particular period or duration agreed to before the nodes are powered down. The synchronization event can also be a combination of time and received wireless synchronization messages. In this case, the wireless nodes wake up the receivers periodically to listen for a synchronization message. The wireless nodes do not start relaying messages until after receiving the network wakeup synchronization message. After a pre-defined period or the receipt of a power-down message, the wireless nodes will power down.

After the transceiver is activated (step 606), the transceiver in a wireless node determine if it has a message to send (step 608). If not, then the transceiver listens for incoming messages (step 610). If there is a message to be sent, the transceiver determines the route to the destination (step 612). The transceiver then waits for available channel (step 614) and when a channel is available, the message is transmitted (step 616). The transceiver waits for receipt confirmation (step 618) from the destination node (step 618). If confirmation is not received within the timeout period (step 620), then the transceiver returns to step 612 and attempt transmission again. If confirmation is received, then the transceiver checks to see if the synchronization has timed out (step 622). If so, the transceiver is powered down (step 624). If synchronization has not yet timed out, then the operation returns to step 608 where the transceiver determines if there is a message to be sent.

Accordingly to another aspect of the present invention, the wireless environmental monitoring and control system can be applied to security applications. Thus, in an alternate embodiment, the sensor nodes are implemented using smoke detectors, infrared (IR) motion detection, ultrasonic presence detection, and security key detection. The actuator nodes can be implemented as alarms, such as a bell alarm or a visual alarm indicator. Detection of the presence of smoke or motion can be transmitted as messages to the actuator nodes so that the events can be reported accordingly.

C. Scheduled Transmission for Power Saving

As described above, the wireless nodes, whether a sensor node or an actuator node, are typically battery powered or solar powered and thus power conservation is critical. In accordance with one aspect of the present invention, a scheduled transmission protocol is implemented in the environmental monitoring and control system for promoting efficient power use and power conservation.

In one embodiment, the receiver nodes schedule all transmission slots. In the present description, the receiver nodes are those wireless nodes receiving transmission of messages. For example, the receiver nodes can be the actuator nodes receiving transmission of sensor data and/or commands from respective sensor nodes. The sensor nodes send message packets at scheduled times and the receiver node responds to transmissions with an acknowledge packet. The acknowledge packet contains the timing information for the sensor nodes' next scheduled packet transmission and the next frequency of transmission (if frequency hopping is used). If the receiver node wants to communicate to the sensor node, the receiver node sends data/command packets to the sensor nodes after receiving packets from the sensor nodes, but before sending the acknowledge packet that terminates the time slot. The benefit of this protocol is that the sensor nodes and receiver nodes can sleep until the next scheduled transmission slot, saving a tremendous amount of power.

Alternately, instead of having the receiver nodes schedule the transmission slots, the sender nodes can also function to provide scheduling of the next transmission. In the present description, the sender nodes are those wireless nodes that are transmitting messages. In this case, the sender nodes send as a message the timing information for the receiver nodes' next scheduled packet transmission. After the receiver nodes receive and acknowledge the message containing the timing information, the sender node and the receiver nodes power down until the next scheduled time slot. Furthermore, the sender node and the receiver node can also negotiate the next scheduled time slot. In one embodiment, either the sender node or the receiver node publishes to the other node its available timeslots. The node receiving the available timeslots information processes the information and compares the information with its own available timeslot. A desired timeslot is selected and the receiving node sends an acknowledgement message to the sending node to confirm the selected timeslot.

Thus, according to the present invention, any pair of wireless nodes that want to communicate with each other can schedule a time slot on an ad hoc basis, depending on the response time requirements of the application. During the communication between a pair of nodes, the nodes determine the start time of the next communication time so that the nodes do not have to use power with their receivers or transmitters on until the next scheduled transmission time. The nodes can turn the power off to the transceiver until the next scheduled transmission time. To further reduce power requirement, wireless nodes should maintain reasonably accurate time bases so that transmissions can be synchronized. The accuracy can be enhanced by timing synchronization packets that are broadcast through the system to all wireless nodes that want to synchronize transmissions. To support global broadcast packets, nodes can schedule a time slot when all nodes are listening. Broadcast packets sent at this time can be received by all nodes listening. To assure all nodes in the network receive the broadcast packets, nodes that receive broadcast packets can re-transmit the broadcast packets for nodes that were not in range of the source of the broadcast packet. Broadcast packets can optionally be acknowledged by the nodes that receive them.

D. Wireless Sensor Probe Configurations

Figure 7:
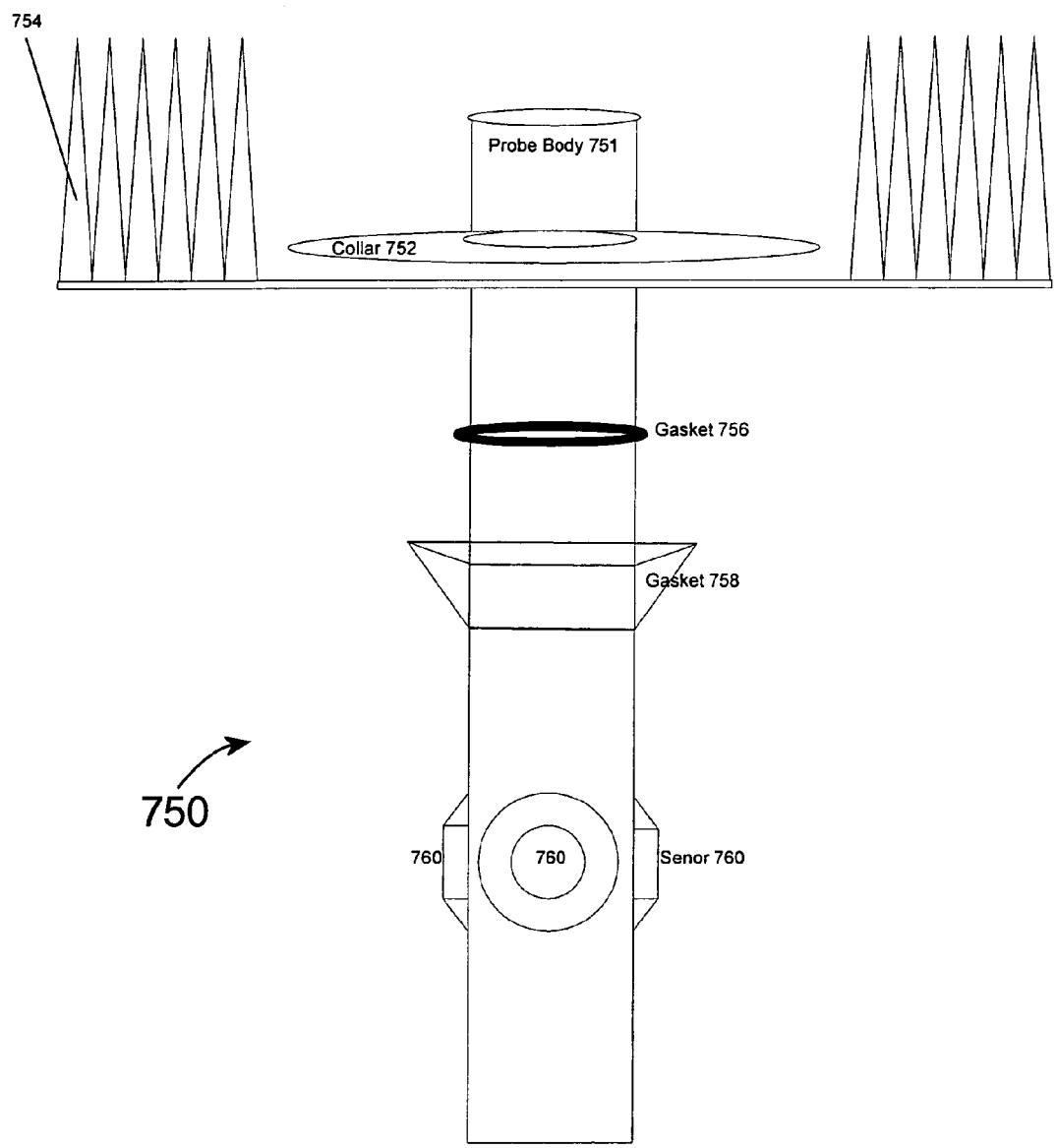
FIG. 7 is a cross-sectional diagram illustrating a sensor node according to one embodiment of the present invention and the installation of the sensor node in the ground.

When the environmental monitoring and control system of the present invention is used for irrigation, it is desirable to have a sensor node that can easily be installed in the ground to measure soil moisture, temperature as well as other properties of the soil and air. FIG. 7 is a cross-sectional diagram illustrating a sensor node according to one embodiment of the present invention and the installation of the sensor node in the ground. Referring to FIG. 7, a sensor node 750 is inserted into the soil. Sensor node 750 includes a collar 752 extends out from the housing or the probe body 751 of the sensor node for anchoring the sensor node above the soil. Also, collar 752 serves to protect the sensor node from encroachment by surrounding plants, reduce the buildup of water around the probe, and reduce grass 754 shading of the probe. Collar 752 may be attached to sensor node 750 or it may be loose or free floating. Sensor node 750 also includes a gasket 756 that extends out from the surface of sensor body 751. Gasket 756 serves to increase the contact force with the surrounding soil improving the stability of the installed sensor node and reducing the possibility that water will flow down along the side of the sensor body. Gasket 756 is in the shape of a ring, such as a rubber ring. In the present embodiment, sensor node 750 further includes a gasket 758. Gasket 758 is a gasket structure with an angular shape. The angular gasket structure has a top portion facing the top of the probe body, a bottom portion facing the bottom of the probe body and a side portion having tapered width where the width decreases from the top portion to the bottom portion. Gasket 758 aids in the insertion of sensor node 750, but prevents the sensor node from being pushed up out of the soil by regular expansion cycles. In other embodiments, the sensor node may include only one gasket.

In the present embodiment, sensor node 750 further includes raised structure 760 for housing the sensor component. The raised structure improves the contact force between the sensor and the soil. The raised structure also improves the stability of the sensor node in the soil.

Figure 8:
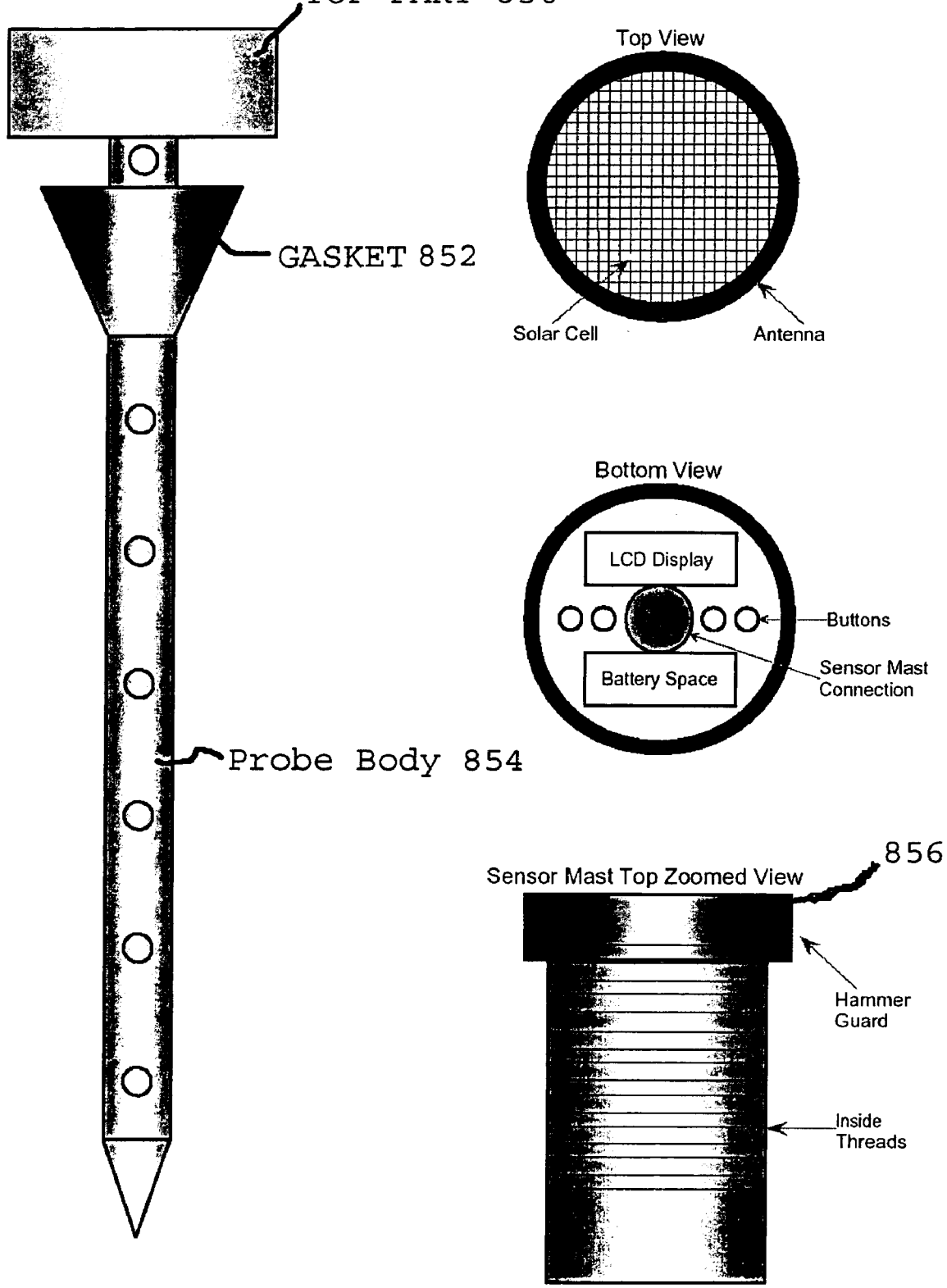
FIGS. 8 and 9 are two embodiments of a sensor node of the present invention constructed using separable probe body.
Figure 9:
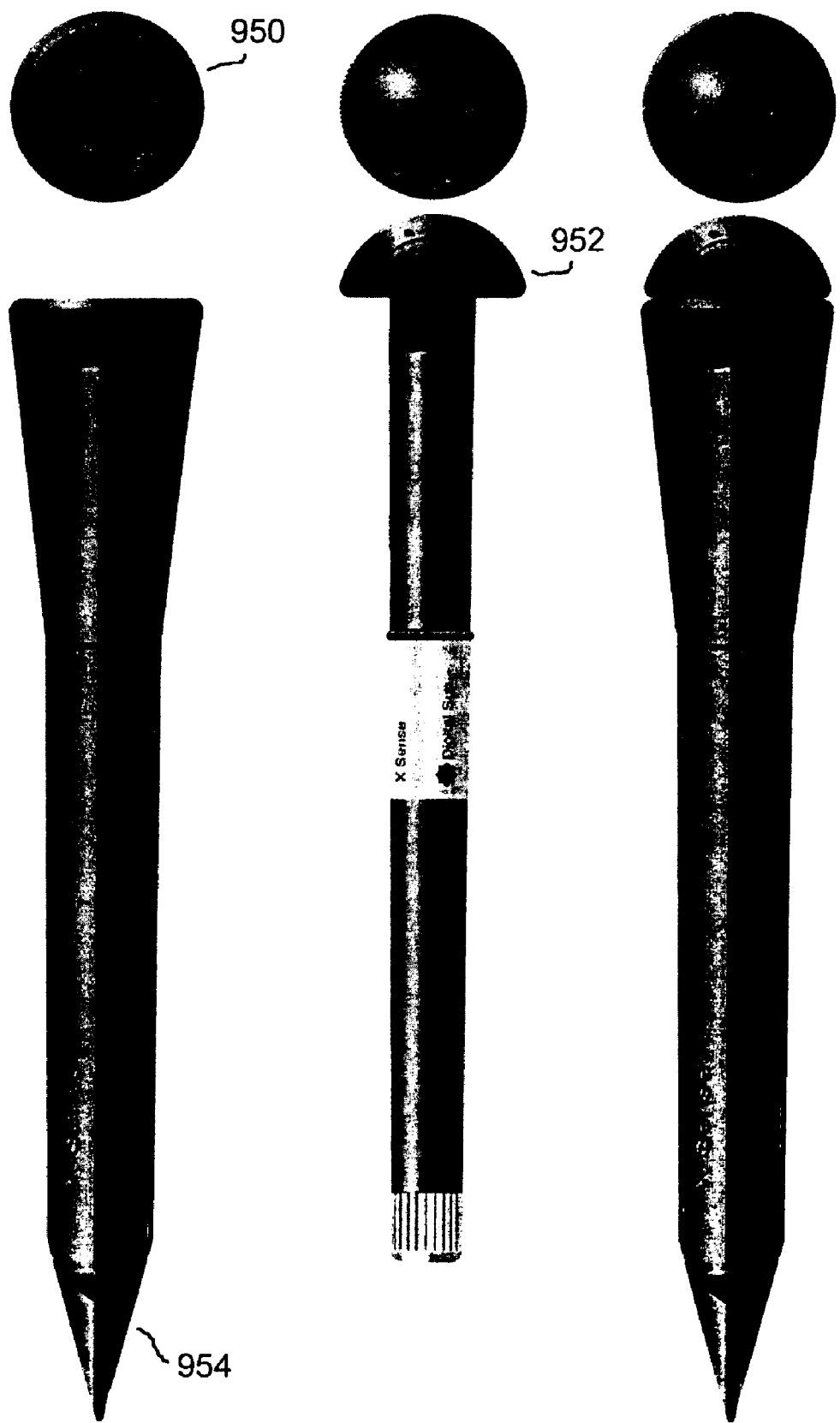

According to another embodiment, the sensor node is implemented using a separable probe body in order to protect sensitive components during installation of the sensor node. FIGS. 8 and 9 are two embodiments of a sensor node of the present invention constructed using separable probe body. Referring to FIG. 8, a sensor node includes a probe body 854 formed with a gasket 852. The probe body can be inserted into the soil before the sensor circuitry, formed in the form of a sensor mast 856 is inserted into probe body 854. The top part 850 of probe body 854 includes solar cells formed on the top and a data display and battery slots on the bottom. The data display can be an LED or an LCD display. A connection to the sensor mast is also provided. Referring to FIG. 9, a sensor node includes a probe body 954 with a top part 950. A sensor mast 952, containing the sensor, the related circuitry and the power circuitry, is formed separate from probe body 954 and can be inserted in probe body 954. During installation, probe body 954, without the sensor mast, is hammered or pressed into the soil. After the probe body insertion is complete, sensor mast 952 can be inserted into probe body 954 to complete the installation. In this manner, the sensor node can be inserted into the soil without damaging the antenna, the solar cells, the electronics or other sensitive components on the sensor mast. A gasket (not shown) can be provided on sensor mast 952 to anchor the sensor mast to the inner perimeter of the probe body and to seal the space between the mast and the probe body. The removable top part 950 can then be put in place to enclose the sensor node. The top part can attach by a screw mount, bayonet type mount, or a flanged mount that allows the electrical connections between the top piece and the probe body to be made automatically. In FIG. 9, top part 950 can further include a LCD display (not shown) for displaying operating data of the sensor.

FIGS. 10A and 10B illustrate differential embodiments of the sensor nodes of the present invention. In FIG. 10A, the top part of the sensor node includes a PC board housing the antenna, the transceiver and the processor circuitry. The battery slot is provided in the body of the sensor mast. In this embodiment, moisture sensors are incorporated in the sensor mast at the bottom of the probe body. In FIG. 10B, the top part of the sensor node includes a PC board housing the antenna, the transceiver and the processor circuitry and a compartment for the battery. A series of moisture sensors are installed in the body of the sensor mast.

In FIGS. 8 and 9, the probe body assumes a circular shape. However, in other embodiment, the sensor body can take other shapes as well to suit the needs of the installation. FIG. 11 illustrates variations on the probe body configuration. Referring to FIG. 11, a rectangular probe body 1100, a hexagonal probe body 1102, a round or circular probe body 1104, a triangular probe body 1106 and a cross-beam probe body 1108 are shown. No matter what the shape the probe body assumes, a collar and a gasket can be used to anchor and secure the sensor node.

The sensor component can be implemented using any suitable sensor types. For example, thin film resistive moisture sensor or thin film capacitive moisture sensor can be used.

E. RF Based Positioning and Intrusion Detection

With an array of wireless network nodes, it is beneficial to know the relative physical position of the nodes to assist in message routing and also to know the location of the actuators and sensors associated with the wireless nodes. According to another aspect of the present invention, the wireless environmental monitoring and control system provides positioning determination by measurement of the RF power received from each node and the RF power sent from each node. Specifically, because RF power drops off by the square of the distance from the source, the measurement of the RF power of a received signal defines a distance radius around the receiver where the source can be located. By triangulating the measured RF power from multiple wireless nodes, the position of the wireless nodes can be determined. In one embodiment, the processor in each wireless node monitors the fall of the power level as the object passes between nodes.

In one embodiment, a wireless node sends out a measurement signal with a message containing the measured transmit power. Each node that receives the measurement signal measures the power and reports it back to the transmitter node. Each node in the network transmits a measurement signal at different times. Each receiving node sends the transmitter node the received power information and the transmitter processes the power information to determine the range of each receiving node. The range information is broadcast back to all receiving nodes. Each node stores the range information from the nodes that it receives data from and uses it to calculate the relative position of each node in the network. To interpret the relative positions into physical positions, it is necessary to know the physical position of at least two nodes in the network. This is used to orient and scale the relative positions.

According to yet another embodiment of the present invention, the environmental monitoring and control system is configured for occupancy detection or intrusion detection. In this embodiment, the RF transceivers of the wireless nodes are used as sensors to detect the movement of objects in the regions between wireless nodes. FIG. 12 is a schematic diagram illustrating the use of the environmental monitoring and control system of the present invention for occupancy detection. Referring to FIG. 12, an object 1220 is in a position between a wireless node 1206 and a wireless node 1212. This position affects the measured RF power level of signals sent between the two nodes. By measuring the RF power levels of signals sent between all of the nodes in the network and identifying large changes, it is possible to estimate the location and motion of objects in the region. The detection can be further enhanced by correlating the measurements of the nodes to reduce false alarms and improve precision of the position estimate. To enhance the quality of the detection, it is desirable to know the physical location of each of the transceivers in the network. This can be measured during installation or automatically estimated from RF power measurements as detailed above.

F. Two-Wire Control of Sprinkler System

According to another aspect of the present invention, a two-wire control system and method for interfacing environmental sensors or other irrigation control data to a timer-based sprinkler controller is described. The two-wire control system allows a wireless sensor network to be incorporated into existing irrigation systems including a central sprinkler controller. The two-wire control system enables precise control over irrigation times for individual zones within a full sprinkler controller cycle. Furthermore, the two-wire control system enables the control of on/off and duration functions for individual zones of an automatic sprinkler controller. In one embodiment, the two-wire control system includes a single relay inserted into the common line return of a timer-based sprinkler controller and a sensing circuit coupled to monitor the voltage or current on the common line. The two-wire control system enables precise control of irrigation durations for individual zones in an irrigation cycle.

Existing automatic sprinkler controllers for residential and commercial applications are typically wired so that the sprinkler controller provides 24VAC drive signals to each valve in the system by switching one side of the two-wire connection to the valve. The other side/wire to the valve is connected together with the "common" line of all other valves. In this setup, each valve in the system has a single independent connection to the controller and another connection that is common with all of the other valves in the system.

When an environment sensor is incorporated in such a sprinkler controller system, the sensor data inputs typically operate to completely override the on/off/zone duration information of the sprinkler controller. For example, if a rain sensor detects rainfall it will completely block the irrigation controller from applying water for a duration determined by the rain sensor. This is typically implemented by inserting a relay into the common path and breaking the circuit to block irrigation cycles and making the circuit to enable irrigation cycles. The conventional sensor data integration method thus operates to disable all zones for the duration.

However, with the two-wire control system of the present invention, it is possible to adjust the on/off and duration of each irrigation zone to provide more precise control of the water applied to a particular zone. This is particularly useful when soil moisture sensors are used or other weather forecasting and control algorithms are used where it is beneficial to be able to adjust the duration as well as the on/off of each irrigation zone.

In one embodiment, the two-wire control system interfaces sensors/auxiliary decision information to an existing automatic sprinkler system so that precise control of on/off and duration of individual zones in an irrigation cycle is attained. FIG. 13 is a block diagram of an automatic sprinkler system 1300 incorporating the two-wire control system according to one embodiment of the present invention. Referring to FIG. 13, sprinkler system 1300 includes a timer-based sprinkler controller 1302. Sprinkler controller 1302 provides irrigation control of zone no. 1 to zone no. N. Thus, sprinkler controller 1302 includes a first set of wires coupled to the zone control nodes 1 to N for providing the 24V drive signal to the respective valves no. 1 to N. A common line 1304 connects a common node 1304 to all the valves for establishing the common return path.

Sprinkler system 1300 includes a two-wire control system 1305 for providing precision on/off or duration control of each irrigation zone controlled by sprinkler controller 1302.

In two-wire control system 1305, a relay 1306 is inserted into the path of common line 1304 to provide on/off control based on sensor or auxiliary control data. Relay 1306 can be provided outside of the housing of sprinkler controller 1302 or within the controller unit itself.

Two-wire control system 1305 further includes a sensing circuit 1308 for monitoring the start and stop cycles of each zone so that the system can precisely switch the individual valves on/off to control the duration within the interval defined by the irrigation controller. In the present embodiment, sensing circuit 1308 is coupled to the common line and the system monitors the start and stop times of each zone by measuring the voltage and/or current on the "common line" of the valves. Specifically, the sensing circuit detects the assertion and deassertion of the valves by measuring the voltage and/or current on the common line of the valves.

In another embodiment, the sensing circuit can be coupled to each of the control line of the zones. The system thus monitors the start and stop times of each zone by measuring the voltage and/or current on each individual control line for the valves. Transitions of voltage and/or current on the "common line" or control lines are used to determine the start/stop of each irrigation zone. Knowing the start and stop time of the control signal for each of the valves enables the control of the relay on the common line to enable each individual zone for any duration within the maximum time for that zone set by the irrigation controller. Two-wire control system 1305 further includes a relay controller 1310 receiving the sensor or auxiliary data input and providing a control signal to relay 1306 for controlling the irrigation cycle of each zone.

FIG. 14 is a timing diagram illustrating the operation of sprinkler system 1300 according to one embodiment of the present invention. In FIG. 14, the control line for zone no. 1 is asserted at time T1 (see curve ZoneCtl#1) and the common line experience an OFF to ON transition. Control system 1305 detects that zone no. 1 is being turned on as triggered by sprinkler controller 1302. Relay controller 1310 determines based on the sensor control data input that zone no. 1 should be turned on for the full duration. Thus, relay controller 1310 turns on relay 1306 so that the valve for zone no. 1 is turned on, as shown by the curve labeled ZONE#1.

At time T2, the control line for zone no. 2 is asserted (see curve ZoneCtl#2) and an OFF to ON transition occurred on the common line. For this irrigation zone, relay controller 1310 determines that the irrigation duration for the zone can be shortened to maintain effective moisture levels. Thus, relay 1306 is only turned on for a short time and is turned off at time T3 which as the effect of turning off the valve for zone no. 2 (see curve ZONE#2). In this manner, two-wire control system 1305 shortens the irrigation cycle for a specific zone.

At time T4, the control line for zone no. 3 is asserted (see curve ZoneCtl#3) and an OFF to ON transition occurred on the common line. For this irrigation zone, relay controller 1310 determines that the irrigation cycle should be terminated entirely. Thus, relay 1306 is not turned on at all and the irrigation cycle for zone no. 3 is entirely disabled (see curve ZONE#3).

At time T5, the control line for zone no. N is asserted (see curve ZoneCtl#N) and an OFF to ON transition occurred on the common line. For this irrigation zone, relay controller 1310 determines that the irrigation duration should be shortened. Thus, relay 1306 is only turned on for a short time and is turned off at time T6 which as the effect of turning off the valve for zone no. N (see curve ZONE#N). The irrigation cycle for zone no. N is thus shortened.

In summary, control system 1305 detects the first transition on the common line (turn-on) or control line, triggered by the irrigation controller to determine the turning-on of a particular zone. The transition can be detected either by detecting discontinuities in the voltage on the common/control lines or by detecting discontinuities in the current through the common/control lines. The next transition on the control lines corresponds to the turning-off of the zone. In this manner, the control system keeps track of the start time and the duration of control signal for each valve. Relay 1306 is thus able to control the interval of each zone from the full duration set by the irrigation controller down to 0 seconds.

In one embodiment, detection of the voltage on the common line or the control lines can be achieved through the use of a transistor or operational amplifier that saturates when the potential difference on the two contacts of the open relay exceed a specified threshold. Detection of the current in the common line or the control lines can be achieved either by an inductively coupled current detector or by measuring the voltage differential across an in-line resistor.

The sensor or auxiliary control data can include data from moisture sensors, temperature sensors, or weather measurement sensors.

According to another embodiment of the present invention, a sprinkler controller can incorporate a relay in series with the common line. In that case, the two-wire control system of the present invention includes a sensing circuit for sensing the on-off duration of each irrigation zone and a relay controller coupled to control the relay in the sprinkler controller based on sensor and auxiliary control data.

Furthermore, according to another embodiment of the present invention, the sensing circuit of the control system is used to learn the programming of the sprinkler controller that is driving the valves. Basically, the sensing circuit enables the control system to learn the start time and the duration of each individual zone in the cycle. For example, irrigation cycles can start at 4:00 AM on Monday, Wednesday and Saturday. This cycle can have independent durations for each zone in the cycle. The controller can also have other programmed cycles that start at a different time, different period and with different durations. For example, an irrigation cycle can start on 10:00 AM every other day and with different durations for each zone. The sensing circuit of the present invention monitors the common line and uses the ON-OFF transitions on the common line to learn the programming of the sprinkler controller over time. The control system can use the sprinkler programming information to determine the best time to enable an irrigation cycle, in addition to the soil moisture and other sensor data.

The above detailed descriptions are provided to illustrate specific embodiments of the present invention and are not intended to be limiting. Numerous modifications and variations within the scope of the present invention are possible. The present invention is defined by the appended claims.

We claim:

1. A wireless sensor probe comprising:
 a probe body for placement into the ground; said probe body having an interior, an exterior, a top and a bottom;
 a stabilizing gasket secured on and extending out from an external side surface of said probe body between said top and bottom of said probe body such that said stabilizing gasket is positioned completely beneath the ground when said wireless sensor probe is inserted into the ground; said stabilizing gasket having an annular shape with a top surface facing a top of said probe body and a side surface increasing in size from a bottom portion of said stabilizing gasket to a top portion of said stabilizing gasket such that said stabilizing gasket allows insertion of said wireless sensor probe into the ground and resists said wireless sensor probe from being moved upwards from said ground;

a mast member including one or more sensor devices for sensing a soil property surrounding the probe body when the probe body is inserted into the ground; and a top member selectively removable from a top of said probe body;

wherein the mast member is configured to removably fit within the interior of the probe body; and, wherein the interior of the probe body is selectively enclosable with the top member; and, wherein the wireless sensor probe is further configured to wirelessly transmit data from the one or more sensor devices.

2. The wireless sensor probe of claim 1, further comprising: a collar situated near a top portion of the probe body.

3. The wireless sensor probe of claim 1, wherein the mast member further comprises a battery.

4. The wireless sensor probe of claim 1, further comprising a wireless transceiver circuit in communication with said sensor devices.

5. The wireless sensor probe of claim 1, wherein the top member connects to the probe body by an arrangement selected from the following: a screw mount, a bayonet type mount and a flange mount.

6. The wireless sensor probe of claim 1, wherein the top member comprises a solar cell panel.

7. The wireless sensor probe of claim 1, wherein the top member comprises a data display.

8. The wireless sensor probe of claim 7, wherein the data display comprises one of an LED display or an LCD display.

9. The wireless sensor probe of claim 1, wherein a shape of the probe body is selected from a round shape, a hexagon shape, a rectangular shape, a triangular shape, and a cross-beam shape.

10. The wireless sensor probe of claim 1, wherein one or more sensor devices further comprise sensor components selected from the following group: an air temperature sensor, a relative humidity sensor, a light level sensor, a soil moisture sensor, a soil temperature sensor, a soil dissolved oxygen sensor, a soil pH sensor, a soil conductivity sensor, and a soil dielectric frequency response sensor.

11. The wireless sensor probe of claim 1, wherein said stabilizing gasket is further positioned so as to minimize flow of water down said probe body.

12. The wireless sensor probe of claim 1, wherein said stabilizing gasket is a rubber ring.

13. A wireless soil sensor having selectively joinable components, the wireless soil sensor comprising:

a probe body having an opening into an interior of the probe body and a top end and a bottom end;

a stabilizing gasket secured to an outer side surface of said probe body so as to prevent flow of water between said stabilizing gasket and said probe body when located completely in the soil; said stabilizing gasket having an annular shape with a top surface facing a top of said probe body and a side surface increasing in width from a bottom portion of said stabilizing gasket to a top portion of said stabilizing gasket such that said stabilizing gasket allows insertion of said wireless soil sensor into the ground and resists said wireless soil sensor from being moved upwards from said ground;

a component mast comprising sensor circuitry; said component mast being user-insertable into the opening into the interior of the probe body; and, a probe top selectively engagable with the probe body so as to cover the opening into the interior of the probe body;

wherein the wireless soil sensor is further configured to wirelessly transmit data from the sensor circuitry; and, wherein said stabilizing gasket is located between said top end and said bottom end of said probe body.

14. The wireless soil sensor of claim 13, wherein the component mast connects to the probe top.

15. The wireless soil sensor of claim 13 further comprising a plurality of sensor components.

16. The wireless soil sensor of claim 15, wherein at least a portion of the plurality of sensor components are positioned along a length of the probe body.

17. The wireless soil sensor of claim 13, wherein the sensor circuitry further comprises sensor components selected from the following group: an air temperature sensor, a relative humidity sensor, a light level sensor, a soil moisture sensor, a soil temperature sensor, a soil dissolved oxygen sensor, a soil pH sensor, a soil conductivity sensor, and a soil dielectric frequency response sensor.

18. The wireless soil sensor of claim 13 wherein the probe top connects to the probe body by an arrangement selected from the following: a screw mount, a bayonet type mount and a flange mount.

19. The wireless soil sensor of claim 13, wherein said component mast further comprises a battery.

20. The wireless soil sensor of claim 13, wherein said probe top further comprises a display.

21. The wireless soil sensor of claim 13, wherein said probe top further comprises a solar cell.

22. The wireless sensor probe of claim 13, wherein said stabilizing gasket is a rubber ring.

23. A wireless sensor probe comprising:

a probe body for placement into the ground; said probe body having an interior, an exterior, a top and a bottom;

a stabilizing gasket secured on an external side surface of said probe body between said top and bottom of said probe body such that said stabilizing gasket is positioned completely beneath the ground when said wireless sensor probe is inserted into the ground; said stabilizing gasket having an annular surface facing a top of said probe body and a side surface decreasing in size from a top portion of said stabilizing gasket to a bottom portion of said stabilizing gasket such that said stabilizing gasket allows insertion of said wireless sensor probe into the ground and resists said wireless sensor probe from being moved upwards from said ground;

a mast member;

one or more sensor devices for sensing a soil property surrounding the probe body when the probe body is inserted into the ground; and a top member selectively removable from a top of said probe body;

wherein the mast member is configured to removably fit within the interior of the probe body; and, wherein the interior of the probe body is selectively enclosable with the top member; and, wherein the wireless sensor probe is further configured to wirelessly transmit data from the one or more sensor devices.

* * * * *